US010822399B2

(12) United States Patent
Keyt et al.

(10) Patent No.: US 10,822,399 B2
(45) Date of Patent: Nov. 3, 2020

(54) IGA MULTI-SPECIFIC BINDING MOLECULES

(71) Applicant: IGM BIOSCIENCES, INC., Mountain View, CA (US)

(72) Inventors: Bruce Keyt, Hillsborough, CA (US); Leonard George Presta, San Francisco, CA (US); Fen Zhang, San Francisco, CA (US); Stephen F. Carroll, Walnut Creek, CA (US)

(73) Assignee: IGM Biosciences, Inc., Mountain View, CA (US)

(*) Notice: Subject to any disclaimer, the term of this patent is extended or adjusted under 35 U.S.C. 154(b) by 0 days.

(21) Appl. No.: 15/117,432

(22) PCT Filed: Feb. 10, 2015

(86) PCT No.: PCT/US2015/015268
§ 371 (c)(1),
(2) Date: Aug. 8, 2016

(87) PCT Pub. No.: WO2015/120474
PCT Pub. Date: Aug. 13, 2015

(65) Prior Publication Data
US 2016/0368971 A1 Dec. 22, 2016

Related U.S. Application Data

(60) Provisional application No. 61/937,984, filed on Feb. 10, 2014.

(51) Int. Cl.
*A61K 39/00* (2006.01)
*C07K 16/12* (2006.01)
*C07K 16/10* (2006.01)
*A61K 47/68* (2017.01)

(52) U.S. Cl.
CPC .......... *C07K 16/1282* (2013.01); *A61K 47/68* (2017.08); *A61K 47/6841* (2017.08); *C07K 16/1018* (2013.01); *C07K 16/1027* (2013.01); *A61K 2039/505* (2013.01); *C07K 2317/24* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 4,815,567 A | 3/1989 | Ikejima | |
| 7,951,378 B2 | 5/2011 | Larrick | |
| 8,377,435 B2 | 2/2013 | Bhat | |
| 9,409,976 B2 | 8/2016 | Teng | |
| 9,458,241 B2 | 10/2016 | Bhat | |
| 9,938,347 B2 | 4/2018 | Wang | |
| 9,951,134 B2 | 4/2018 | Keyt | |
| 10,351,631 B2 | 7/2019 | Keyt | |
| 10,400,038 B2 | 9/2019 | Keyt | |
| 10,570,191 B2 | 2/2020 | Keyt | |
| 10,604,559 B2 | 3/2020 | Carroll | |
| 10,618,978 B2 | 4/2020 | Keyt | |
| 10,689,449 B2 | 6/2020 | Wang et al. | |
| 2005/0249723 A1* | 11/2005 | Lazar | C07K 16/00 424/133.1 |
| 2005/0287150 A1 | 12/2005 | Ambrosino et al. | |
| 2010/0015044 A1 | 1/2010 | Qiu | |
| 2011/0014182 A1* | 1/2011 | Alard | C07K 16/18 424/130.1 |
| 2011/0274702 A1 | 11/2011 | Lanzavecchia | |
| 2013/0280167 A1 | 10/2013 | Rodriguez | |
| 2014/0120113 A1 | 5/2014 | Hendrikus et al. | |
| 2018/0009897 A1 | 1/2018 | Wang | |
| 2018/0118814 A1 | 5/2018 | Carroll | |
| 2018/0265596 A1 | 9/2018 | Keyt | |
| 2019/0002566 A1 | 1/2019 | Keyt | |
| 2019/0100597 A1 | 4/2019 | Keyt | |
| 2019/0185570 A1 | 6/2019 | Keyt | |
| 2019/0330360 A1 | 10/2019 | Wang | |
| 2019/0330374 A1 | 10/2019 | Wang | |
| 2019/0338031 A1 | 11/2019 | Keyt | |
| 2019/0338040 A1 | 11/2019 | Keyt | |
| 2019/0338041 A1 | 11/2019 | Baliga | |
| 2020/0190190 A1 | 6/2020 | Keyt | |
| 2020/0239572 A1 | 7/2020 | Baliga | |
| 2020/0255546 A1 | 8/2020 | Keyt | |

FOREIGN PATENT DOCUMENTS

| | | |
|---|---|---|
| CN | 101643512 | 2/2010 |
| CN | 102989018 | 3/2013 |
| CN | 103429260 | 12/2013 |
| JP | 2006515503 | 6/2006 |
| JP | 2007533330 | 11/2007 |

(Continued)

OTHER PUBLICATIONS

Atwell et al., "Stable heterodimers from remodeling the domain interface of a homodimer using a phage display library," J. Mol. Biol. 1997, vol. 270, pp. 26-35.

Babcock et al., "Human monoclonal antibodies directed against toxins A and B prevent Clostridium difficile-induced mortality in hamsters," Infect Immun. 2006 vol. 74, No. 11, pp. 6339-6347.

Bakema et al., "Immunoglobulin A," mABs 2011, vol. 3, No. 4, pp. 352-361.

Clackson et al., "Making antibody fragments using phage display libraries," Nature, 1991, vol. 352, pp. 624-628.

Dechant et al., "Effector mechanisms of recombinant IgA antibodies against epidermal growth factor receptor," J. Immunology 2007, vol. 179, No. 5, pp. 2936-2943.

(Continued)

*Primary Examiner* — Jana A Hines
*Assistant Examiner* — Khatol S Shahnan Shah

(57) ABSTRACT

The present invention concerns IgA multi-specific binding molecules. In particular, the invention concerns multi-specific, including bispecific, binding molecules comprising IgA heavy chain sequences, and methods for their preparation and use.

17 Claims, 4 Drawing Sheets
Specification includes a Sequence Listing.

(56) References Cited

FOREIGN PATENT DOCUMENTS

| | | |
|---|---|---|
| JP | 2008512987 | 5/2008 |
| JP | 2010531890 | 9/2010 |
| WO | WO 1991/016074 A1 | 9/1991 |
| WO | WO 1996/027011 A1 | 9/1996 |
| WO | 2004009618 | 1/2004 |
| WO | 2006008548 | 1/2006 |
| WO | 2006052641 | 5/2006 |
| WO | 2006121422 | 11/2006 |
| WO | WO 2008/028946 A2 | 3/2008 |
| WO | 2009003019 | 12/2008 |
| WO | 2009/055711 A2 | 4/2009 |
| WO | WO 2010/130363 A1 | 11/2010 |
| WO | WO 2011/117848 A1 | 9/2011 |
| WO | WO 2012/123949 A1 | 9/2012 |
| WO | 2013007770 | 1/2013 |
| WO | 2013120012 | 8/2013 |
| WO | 2015053887 | 4/2015 |
| WO | 2015153912 | 10/2015 |
| WO | 2016118641 | 7/2016 |
| WO | 2016141303 | 9/2016 |
| WO | 2016154593 | 9/2016 |
| WO | 2016168758 | 10/2016 |
| WO | 2017059380 | 4/2017 |
| WO | 2017059387 | 4/2017 |
| WO | 2017196867 | 11/2017 |
| WO | 2018017761 | 1/2018 |
| WO | 2018017763 | 1/2018 |
| WO | 2018017888 | 1/2018 |
| WO | 2018017889 | 1/2018 |
| WO | 2018187702 | 10/2018 |
| WO | 2019165340 | 8/2019 |
| WO | 2019169314 | 9/2019 |
| WO | 2020086745 | 4/2020 |
| WO | 2020163646 | 8/2020 |

OTHER PUBLICATIONS

Ellman, "Biosynthetic method for introducing unnatural amino acids site-specifically into proteins," Meth. Enzym. 1991, vol. 202, pp. 301-336.
Giesse et al., "Eukaryotic expression systems: a comparison," Protein Expr. Purif. 1996, vol. 8, pp. 271-282.
He et al., "Broadly neutralizing anti-influenza virus antibodies: enhancement of neutralizing potency in polyclonal mixtures and IgA backbones," J Virol. 2015 vol. 89, No. 7, pp. 3610-3618.
Urnovitz et al., "IgA: IgM and IgA:IgA hybrid hybridomas secrete heteropolymeric immunoglobulins that are polyvalent and bispecific," J. Immunology 1988, vol. 140, No. 2, pp. 558-563.
Johansen et al. "The J chain is essential for polymeric Ig receptor-mediated epithelial transport of IgA," J Immunol. Nov. 1, 2001;167(9):5185-92.
Jones et al., "Replacing the complementarity-determining regions in a human antibody with those from a mouse," Nature 1986, vol. 321, pp. 522-525.
Kaufman, R. J., "Overview of vector design for mammalian gene expression.," Mol. Biotechnol. 2000, vol. 16, No. 2, pp. 151-161.
Kohler et al., "Continuous cultures of fused cells secreting antibody of predefined specificity," Nature, 1975, vol. 256, p. 495.
Makrides, S.C., "Components of vectors for gene transfer and expression in mammalian cells," Protein Expr. Purif. 1999, vol. 17, pp. 183-202.
Marks et al., "By-passing immunization. Human antibodies from V-gene libraries displayed on phage," J. Mol. Biol. 1991, vol. 222, pp. 581-597.
Merchant et al., "An efficient route to human bispecific IgG," Nat Biotechnol 1998, vol. 16, pp. 677-681.
Morrison et al., "Chimeric human antibody molecules: mouse antigen-binding domains with human constant region domains," PNAS 1984, vol. 81, pp. 6851-6855.
Mostov, K.E., "Transepithelial transport of immunoglobulins," Annu Rev Immunol. 1994 vol. 12, pp. 63-84.
Noren et al., "A general method for site-specific incorporation of unnatural amino acids into proteins," Science 1989, vol. 244, p. 182-188.
Ponders and Richards, "Tertiary templates for proteins. Use of packing criteria in the enumeration of allowed sequences for different structural classes," J. Mol. Biol., 1987, vol. 193, pp. 775-791.
Presta, "Antibody engineering," Curr. Op. Struct. Biol. 1992, vol. 2, pp. 593-596.
Putnam, et al., "Primary structure of a human IgA1 immunoglobulin. IV. Streptococcal IgA1 protease, digestion, Fab and Fc fragments, and the complete amino acid sequence of the alpha 1 heavy chain," J Biol Chem. 1979 vol. 254, No. 8, pp. 2865-2874.
Ramsland et al., "Structural basis for evasion of IgA immunity by *Staphylococcus aureus* revealed in the complex of SSL7 with Fc of human IgA1," PNAS 2007 vol. 104, No. 38, pp. 15051-15056.
Ridgeway, et al., "'Knobs-into-holes' engineering of antibody CH3 domains for heavy chain heterodimerization," Protein Eng. 1996 vol. 9, No. 7, pp. 617-621.
Riechmann et al., "Reshaping human antibodies for therapy," Nature 1988, vol. 332, pp. 323-329.
Schaefer et al., "Immunoglobulin domain crossover as a generic approach for the production of bispecific IgG antibodies," PNAS 2011, vol. 108, No. 27, pp. 11187-11192.
Skehel et al., "Receptor binding and membrane fusion in virus entry: the influenza hemagglutinin," Annu Rev Biochem. 2000, vol. 69, pp. 531-569.
Takahashi et al., "Structure of human immunoglobulin gamma genes: implications for evolution of a gene family," Cell. 1982 vol. 29, No. 2, pp. 671-679.
Werner, R. G., "Appropriate mammalian expression systems for biopharmaceuticals," Drug Res. 1998, vo. 48, pp. 870-880.
Wilson et al., "Structure of the haemagglutinin membrane glycoprotein of influenza virus at 3 A resolution," Nature 1981 vol. 289, No. 5796, pp. 366-373.
Zhu et al., "Remodeling domain interfaces to enhance heterodimer formation," Prot. Sci. 1997, vol. 6, 781-788.
Accession No. 0506249A, Primary structure of a human IgA1 immunoglobulin. I. Isolation, composition, and amino acid sequence of the chymotryptic peptides Ig Aalpha1 Bur., PRI Nov. 19, 1996.
Liu, et al., (1979), "Primary Structure of a Human IgA1 Immunoglobulin", The Journal of Biological Chemistry, vol. 254, No. 8, 2839-2849.
Accession No. 4KVN_L, Chain L, Crystal Structure of Fab 39.29 in Complex With Influenza Hemagglutinin A/perth/16/2009 (h3n2), Database PDB [online], Aug. 7, 2013.
Accession No. 4KVN_H, Chain H, Crystal Structure of Fab 39.29 in Complex With Influenza Hemagglutinin A/perth/16/2009 (h3n2), Database PDB [online], Aug. 7, 2013.
Castro, C., et al., (2014), "Putting J chain back on the map: how might its expression define plasma cell development?", The Journal of Immunology, 193: 3248-3255.
Duramad, O., et al., (2014), "IGM-55.5, a novel monoclonal human recombinant IgM antibody with potent activity against B cell leukemia and lymphoma", IGM Biosciences, Inc.—Research and Development SRI International—Cancer Pharmacology, Stanford—Department of Obstetrics and Gynecology, Abstract No. 645, AACR Annual Meeting Apr. 5-9, 2014, San Diego CA.
Hensel, F., et al., (2013), "Early development of PAT-SM6 for the treatment of melanoma", Melanoma Research, 23(4): 264-275.
Rasche, L., et al., (2015), "GRP78-directed immunotherapy in relapsed or refractory multiple myeloma—results from a phase 1 trial with the monoclonal immunoglobulin M antibody PAT-SM6", Haematologica, 100(3): 377-384.

\* cited by examiner

Constant domains  CG1/CA1

```
          1          10         20         30         40         50         60
          *          *          *          *          *          *          *
CG1       ASTKGPSVFPLAPSSKSTSGGTAALGCLVKDYFP-EPVTVSWNSGALTSGVHTFP--AVLQSS
          120        130        140        150        160        170        180
          *          *          *          *          *          *          *
CA1-1     ASPTSPKVFPLSLCSTQPDG-NVVIACLVQGFFPQEPLSVTWSESGQGVTARNFPPSQDASGD
CA2-1     ASPTSPKVFPLSLDSTPQDG-NVVVACLVQGFFPQEPLSVTWSESGQNVTARNFPPSQDASGD 70         80         90         100    (hinge)
          *          *          *          *
CG1       GLYSLSSVVTVPSSSLGTQTYICNVNHKPSNTKVDKKV--EPKSCDKTHTCPPCP
          190        200        210        220        230
          *          *          *          *          *
CA1-1     LYTTSSQLTLPATQCLAGKSVTCHVKHYTNPSQDVTVPCPVPSTPPTPSPSTPPT
CA2-1     LYTTSSQLTLPATQCPDGKSVTCHVKHYTNPSQDVTVPCPVPPPPP--------
```

FIG. 2A

Constant domains CG2/CA2

```
              240        250        260        270        280        290
               *          *          *          *          *          *
CG2     APELLGGPSVFLFPPKPKDTLMISRTPEVTCVVVDVSHEDPEVKFNWYVDGVEVHNAKTKP
              240        250        260        270        280        290
               *          *          *          *          *          *
CA1-2   PSPSCCHPRLSLHRPALEDL-LLGSEANLTCTLTGLRDAS-GVTFTWTPSSGKSAVQG---
CA2-2   ----CCHPRLSLHRPALEDL-LLGSEANLTCTLTGLRDAS-GATFTWTPSSGKSAVQG---

300        310        320        330        340
               *          *          *          *          *
CG2     REEQY-NSTYRVVSVLTVLHQDWLNGKEYKCKVSNKALPAPIEKTISKAK
              300        310        320        330        340
               *          *          *          *          *
CA1-2   PPERDLCGCYSVSSVLPGCAEPWNHGKTFTCTAAYPESKTPLTATLSKS-
CA2-2   PPERDLCGCYSVSSVLPGCAQPWNHGETFTCTAAHPELKTPLTANITKS-
```

FIG. 2B

Constant domains CG3/CA3

```
              350        360        370        380        390        400
                *          *          *          *          *          *
CG3      GQPREPQVYTLPPSRDELTK-NQVSLTCLVKGFYPSDIAVEWESNGQPENN--YKTTPPVLDS-
              350        360        370        380        390        400
                *          *          *          *          *          *
CA1-3    GNTFRPEVHLLPPPSEELALNELVTLTCLARGFSPKDVLVRWLQGSQELPREKYLTWASRQEPS
CA2-3    GNTFRPEVHLLPPPSEELALNELVTLTCLARGFSPKDVLVRWLQGSQELPREKYLTWASRQEPS 410        420        430        440
                *          *          *          *
CG3      --DGSFFLYSKLTVDKSRWQQGNVFSCSVMHEALHNHYTQKSLSLSPGK
              410        420        430        440        450        460        470
                *          *          *          *          *          *          *
CA1-3    QGTTFAVTSILRVAAEDWKKGDTFSCMVGHEALPLAFTQKTIDRLAGKPTHVNVSVVMAEVDGTCY
CA2-3    QGTTFAVTSILRVAAEDWKKGDTFSCMVGHEALPLAFTQKTIDRMAGKPTHVNVSVVMAEVDGTCY
```

FIG. 2C

SEQUENCE LISTING

<160> NUMBER OF SEQ ID NOS: 27

<210> SEQ ID NO 1
<211> LENGTH: 353
<212> TYPE: PRT
<213> ORGANISM: Homo sapiens

<400> SEQUENCE: 1

```
Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr
```

<210> SEQ ID NO 2
<211> LENGTH: 340
<212> TYPE: PRT
<213> ORGANISM: Homo sapiens

<400> SEQUENCE: 2

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
            20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
            115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
            195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
            275                 280                 285

Ala Glu Asp Trp Lys Lys Gly Asp Thr Phe Ser Cys Met Val Gly His
290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 3
<211> LENGTH: 159
<212> TYPE: PRT
<213> ORGANISM: Homo sapiens

<400> SEQUENCE: 3

| Met | Lys | Asn | His | Leu | Leu | Phe | Trp | Gly | Val | Leu | Ala | Val | Phe | Ile | Lys |
| 1 | | | | 5 | | | | | 10 | | | | | 15 | |

| Ala | Val | His | Val | Lys | Ala | Gln | Glu | Asp | Glu | Arg | Ile | Val | Leu | Val | Asp |
| | | | 20 | | | | | 25 | | | | | 30 | | |

| Asn | Lys | Cys | Lys | Cys | Ala | Arg | Ile | Thr | Ser | Arg | Ile | Ile | Arg | Ser | Ser |
| | | 35 | | | | | 40 | | | | | 45 | | | |

| Glu | Asp | Pro | Asn | Glu | Asp | Ile | Val | Glu | Arg | Asn | Ile | Arg | Ile | Ile | Val |
| | 50 | | | | | 55 | | | | | 60 | | | | |

| Pro | Leu | Asn | Asn | Arg | Glu | Asn | Ile | Ser | Asp | Pro | Thr | Ser | Pro | Leu | Arg |
| 65 | | | | | 70 | | | | | 75 | | | | | 80 |

| Thr | Arg | Phe | Val | Tyr | His | Leu | Ser | Asp | Leu | Cys | Lys | Lys | Cys | Asp | Pro |
| | | | | 85 | | | | | 90 | | | | | 95 | |

| Thr | Glu | Val | Glu | Leu | Asp | Asn | Gln | Ile | Val | Thr | Ala | Thr | Gln | Ser | Asn |
| | | | 100 | | | | | 105 | | | | | 110 | | |

| Ile | Cys | Asp | Glu | Asp | Ser | Ala | Thr | Glu | Thr | Cys | Tyr | Thr | Tyr | Asp | Arg |
| | | 115 | | | | | 120 | | | | | 125 | | | |

| Asn | Lys | Cys | Tyr | Thr | Ala | Val | Val | Pro | Leu | Val | Tyr | Gly | Gly | Glu | Thr |
| | 130 | | | | | 135 | | | | | 140 | | | | |

| Lys | Met | Val | Glu | Thr | Ala | Leu | Thr | Pro | Asp | Ala | Cys | Tyr | Pro | Asp |
| 145 | | | | | 150 | | | | | 155 | | | | |

<210> SEQ ID NO 4
<211> LENGTH: 340
<212> TYPE: PRT
<213> ORGANISM: Homo sapiens

<400> SEQUENCE: 4

| Ala | Ser | Pro | Thr | Ser | Pro | Lys | Val | Phe | Pro | Leu | Ser | Leu | Asp | Ser | Thr |
| 1 | | | | 5 | | | | | 10 | | | | | 15 | |

| Pro | Gln | Asp | Gly | Asn | Val | Val | Val | Ala | Cys | Leu | Val | Gln | Gly | Phe | Phe |
| | | | 20 | | | | | 25 | | | | | 30 | | |

| Pro | Gln | Glu | Pro | Leu | Ser | Val | Thr | Trp | Ser | Glu | Ser | Gly | Gln | Asn | Val |
| | | 35 | | | | | 40 | | | | | 45 | | | |

| Thr | Ala | Arg | Asn | Phe | Pro | Pro | Ser | Gln | Asp | Ala | Ser | Gly | Asp | Leu | Tyr |
| | 50 | | | | | 55 | | | | | 60 | | | | |

| Thr | Thr | Ser | Ser | Gln | Leu | Thr | Leu | Pro | Ala | Thr | Gln | Cys | Pro | Asp | Gly |
| 65 | | | | | 70 | | | | | 75 | | | | | 80 |

| Lys | Ser | Val | Thr | Cys | His | Val | Lys | His | Tyr | Thr | Asn | Pro | Ser | Gln | Asp |
| | | | | 85 | | | | | 90 | | | | | 95 | |

| Val | Thr | Val | Pro | Cys | Pro | Val | Pro | Pro | Pro | Pro | Cys | Cys | His | Pro |
| | | | 100 | | | | | 105 | | | | | 110 | | |

| Arg | Leu | Ser | Leu | His | Arg | Pro | Ala | Leu | Glu | Asp | Leu | Leu | Leu | Gly | Ser |
| | | 115 | | | | | 120 | | | | | 125 | | | |

| Glu | Ala | Asn | Leu | Thr | Cys | Thr | Leu | Thr | Gly | Leu | Arg | Asp | Ala | Ser | Gly |
| | 130 | | | | | 135 | | | | | 140 | | | | |

| Ala | Thr | Phe | Thr | Trp | Thr | Pro | Ser | Ser | Gly | Lys | Ser | Ala | Val | Gln | Gly |
| 145 | | | | | 150 | | | | | 155 | | | | | 160 |

| Pro | Pro | Glu | Arg | Asp | Leu | Cys | Gly | Cys | Tyr | Ser | Val | Ser | Ser | Val | Leu |
| | | | | 165 | | | | | 170 | | | | | 175 | |

| Pro | Gly | Cys | Ala | Gln | Pro | Trp | Asn | His | Gly | Glu | Thr | Phe | Thr | Cys | Thr |
| | | | 180 | | | | | 185 | | | | | 190 | | |

| Ala | Ala | His | Pro | Glu | Leu | Lys | Thr | Pro | Leu | Thr | Ala | Asn | Ile | Thr | Lys |
| | | 195 | | | | | 200 | | | | | 205 | | | |

```
Ser Gly Asn Thr Phe Arg Pro Glu Val Glu Leu Met Pro Pro Ser
    210                 215                 220
Glu Glu Leu Ala Leu Asn Glu Leu Val Thr Leu Trp Cys Leu Ala Arg
225                 230                 235                 240
Gly Phe Ser Pro Lys Asp Val Leu Val Arg Trp Leu Gln Gly Ser Gln
                245                 250                 255
Glu Leu Pro Arg Glu Lys Tyr Leu Thr Trp Ala Ser Arg Gln Glu Pro
            260                 265                 270
Ser Gln Gly Thr Thr Thr Phe Ala Val Thr Ser Ile Leu Arg Val Ala
        275                 280                 285
Ala Glu Asp Trp Lys Lys Gly Asp Thr Phe Ser Cys Met Val Gly His
290                 295                 300
Glu Ala Leu Pro Leu Ala Phe Thr Gln Lys Thr Ile Asp Arg Leu Ala
305                 310                 315                 320
Gly Lys Pro Thr His Val Asn Val Ser Val Val Met Ala Glu Val Asp
                325                 330                 335
Gly Thr Cys Tyr
            340

<210> SEQ ID NO 5
<211> LENGTH: 340
<212> TYPE: PRT
<213> ORGANISM: Homo sapiens

<400> SEQUENCE: 5

Ala Ser Pro Thr Ser Pro Lys Val Phe Pro Leu Ser Leu Asp Ser Thr
1               5                   10                  15
Pro Gln Asp Gly Asn Val Val Val Ala Cys Leu Val Gln Gly Phe Phe
                20                  25                  30
Pro Gln Glu Pro Leu Ser Val Thr Trp Ser Glu Ser Gly Gln Asn Val
            35                  40                  45
Thr Ala Arg Asn Phe Pro Pro Ser Gln Asp Ala Ser Gly Asp Leu Tyr
        50                  55                  60
Thr Thr Ser Ser Gln Leu Thr Leu Pro Ala Thr Gln Cys Pro Asp Gly
65                  70                  75                  80
Lys Ser Val Thr Cys His Val Lys His Tyr Thr Asn Pro Ser Gln Asp
                85                  90                  95
Val Thr Val Pro Cys Pro Val Pro Pro Pro Pro Cys Cys His Pro
                100                 105                 110
Arg Leu Ser Leu His Arg Pro Ala Leu Glu Asp Leu Leu Leu Gly Ser
            115                 120                 125
Glu Ala Asn Leu Thr Cys Thr Leu Thr Gly Leu Arg Asp Ala Ser Gly
        130                 135                 140
Ala Thr Phe Thr Trp Thr Pro Ser Ser Gly Lys Ser Ala Val Gln Gly
145                 150                 155                 160
Pro Pro Glu Arg Asp Leu Cys Gly Cys Tyr Ser Val Ser Ser Val Leu
                165                 170                 175
Pro Gly Cys Ala Gln Pro Trp Asn His Gly Glu Thr Phe Thr Cys Thr
            180                 185                 190
Ala Ala His Pro Glu Leu Lys Thr Pro Leu Thr Ala Asn Ile Thr Lys
        195                 200                 205
Ser Gly Asn Thr Phe Arg Pro Glu Val His Leu Leu Pro Pro Ser
    210                 215                 220
Arg Glu Leu Ala Leu Asn Glu Leu Val Thr Leu Gly Cys Leu Ala Arg
225                 230                 235                 240
```

```
Gly Phe Ser Pro Lys Asp Val Leu Val Arg Trp Leu Gln Gly Ser Gln
            245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Ile Ser Ile Leu Arg Val Ala
            275                 280                 285

Ala Glu Asp Trp Lys Lys Gly Asp Thr Phe Ser Cys Met Val Gly His
305         290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Val Met Ala Glu Val Asp
                    325                 330                 335

Gly Thr Cys Tyr
            340

<210> SEQ ID NO 6
<211> LENGTH: 107
<212> TYPE: PRT
<213> ORGANISM: Homo sapiens

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 7
<211> LENGTH: 106
<212> TYPE: PRT
<213> ORGANISM: Homo sapiens

<400> SEQUENCE: 7

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 8
<211> LENGTH: 342
<212> TYPE: PRT
<213> ORGANISM: Homo sapiens

<400> SEQUENCE: 8

Ser Ser Ala Ser Pro Thr Ser Pro Lys Val Phe Pro Leu Ser Leu Asp
1               5                   10                  15

Ser Thr Pro Gln Asp Gly Asn Val Val Ala Cys Leu Val Gln Gly
            20                  25                  30

Phe Phe Pro Gln Glu Pro Leu Ser Val Thr Trp Ser Glu Ser Gly Gln
            35                  40                  45

Asn Val Thr Ala Arg Asn Phe Pro Pro Ser Gln Asp Ala Ser Gly Asp
        50                  55                  60

Leu Tyr Thr Thr Ser Ser Gln Leu Thr Leu Pro Ala Thr Gln Cys Pro
65                  70                  75                  80

Asp Gly Lys Ser Val Thr Cys His Val Lys His Tyr Thr Asn Pro Ser
                85                  90                  95

Gln Asp Val Thr Val Pro Cys Pro Val Pro Pro Pro Pro Cys Cys
            100                 105                 110

His Pro Arg Leu Ser Leu His Arg Pro Ala Leu Glu Asp Leu Leu Leu
        115                 120                 125

Gly Ser Glu Ala Asn Leu Thr Cys Thr Leu Thr Gly Leu Arg Asp Ala
    130                 135                 140

Ser Gly Ala Thr Phe Thr Trp Thr Pro Ser Ser Gly Lys Ser Ala Val
145                 150                 155                 160

Gln Gly Pro Pro Glu Arg Asp Leu Cys Gly Cys Tyr Ser Val Ser Ser
                165                 170                 175

Val Leu Pro Gly Cys Ala Gln Pro Trp Asn His Gly Glu Thr Phe Thr
            180                 185                 190

Cys Thr Ala Ala His Pro Glu Leu Lys Thr Pro Leu Thr Ala Asn Ile
        195                 200                 205

Thr Lys Ser Gly Asn Thr Phe Arg Pro Glu Val His Leu Leu Pro Pro
    210                 215                 220

Pro Ser Arg Glu Leu Ala Leu Asn Glu Leu Val Thr Leu Gly Cys Leu
225                 230                 235                 240

Ala Arg Gly Phe Ser Pro Lys Asp Val Leu Val Arg Trp Leu Gln Gly
                245                 250                 255

Ser Gln Glu Leu Pro Arg Glu Lys Tyr Leu Thr Trp Ala Ser Arg Gln
            260                 265                 270

Glu Pro Ser Gln Gly Thr Thr Thr Phe Ala Val Ile Ser Ile Leu Arg
        275                 280                 285

Val Ala Ala Glu Asp Trp Lys Lys Gly Asp Thr Phe Ser Cys Met Val
    290                 295                 300

Gly His Glu Ala Leu Pro Leu Ala Phe Thr Gln Lys Thr Ile Asp Arg
305                 310                 315                 320

Leu Ala Gly Lys Pro Thr His Val Asn Val Ser Val Val Met Ala Glu
                325                 330                 335

Val Asp Gly Thr Cys Tyr
            340

<210> SEQ ID NO 9
<211> LENGTH: 107
<212> TYPE: PRT

<213> ORGANISM: Homo sapiens

<400> SEQUENCE: 9

```
Ala Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 10
<211> LENGTH: 465
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Tyr Trp Gly Trp Ile Arg Gln Pro Pro Gly Lys Gly Leu Glu
        35                  40                  45

Trp Ile Ala Ser Ile His Asp Ser Gly Ser Ile Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Leu Val Trp Phe Gly Glu Leu Arg Asn Asn Trp Phe
            100                 105                 110

Asp Pro Trp Gly Gln Gly Thr Leu Val Thr Val Ala Ser Ala Ser Pro
        115                 120                 125

Thr Ser Pro Lys Val Phe Pro Leu Ser Leu Asp Ser Thr Pro Gln Asp
    130                 135                 140

Gly Asn Val Val Val Ala Cys Leu Val Gln Gly Phe Phe Pro Gln Glu
145                 150                 155                 160

Pro Leu Ser Val Thr Trp Ser Glu Ser Gly Gln Asn Val Thr Ala Arg
                165                 170                 175

Asn Phe Pro Pro Ser Gln Asp Ala Ser Gly Asp Leu Tyr Thr Thr Ser
            180                 185                 190

Ser Gln Leu Thr Leu Pro Ala Thr Gln Cys Pro Asp Gly Lys Ser Val
        195                 200                 205

Thr Cys His Val Lys His Tyr Thr Asn Pro Ser Gln Asp Val Thr Val
    210                 215                 220
```

```
Pro Cys Pro Val Pro Pro Pro Cys Cys His Pro Arg Leu Ser
225                 230                 235                 240

Leu His Arg Pro Ala Leu Glu Asp Leu Leu Gly Ser Glu Ala Asn
                245                 250                 255

Leu Thr Cys Thr Leu Thr Gly Leu Arg Asp Ala Ser Gly Ala Thr Phe
            260                 265                 270

Thr Trp Thr Pro Ser Ser Gly Lys Ser Ala Val Gln Gly Pro Pro Glu
            275                 280                 285

Arg Asp Leu Cys Gly Cys Tyr Ser Val Ser Val Leu Pro Gly Cys
        290                 295                 300

Ala Gln Pro Trp Asn His Gly Glu Thr Phe Thr Cys Thr Ala Ala His
305                 310                 315                 320

Pro Glu Leu Lys Thr Pro Leu Thr Ala Asn Ile Thr Lys Ser Gly Asn
                325                 330                 335

Thr Phe Arg Pro Glu Val Glu Leu Met Pro Pro Ser Glu Glu Leu
            340                 345                 350

Ala Leu Asn Glu Leu Val Thr Leu Trp Cys Leu Ala Arg Gly Phe Ser
                355                 360                 365

Pro Lys Asp Val Leu Val Arg Trp Leu Gln Gly Ser Gln Glu Leu Pro
370                 375                 380

Arg Glu Lys Tyr Leu Thr Trp Ala Ser Arg Gln Glu Pro Ser Gln Gly
385                 390                 395                 400

Thr Thr Thr Phe Ala Val Thr Ser Ile Leu Arg Val Ala Ala Glu Asp
                405                 410                 415

Trp Lys Lys Gly Asp Thr Phe Ser Cys Met Val Gly His Glu Ala Leu
                420                 425                 430

Pro Leu Ala Phe Thr Gln Lys Thr Ile Asp Arg Leu Ala Gly Lys Pro
            435                 440                 445

Thr His Val Asn Val Ser Val Val Met Ala Glu Val Asp Gly Thr Cys
            450                 455                 460

Tyr
465

<210> SEQ ID NO 11
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln His Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Phe Gly Pro Gly Thr Lys Val Asp Leu Lys Arg Thr Val Ala Ala Pro
```

```
                100                 105                 110
Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 12
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Ser Ser Ala Ser Pro Thr
            100                 105                 110

Ser Pro Lys Val Phe Pro Leu Ser Leu Asp Ser Thr Pro Gln Asp Gly
        115                 120                 125

Asn Val Val Ala Cys Leu Val Gln Gly Phe Phe Pro Gln Glu Pro
    130                 135                 140

Leu Ser Val Thr Trp Ser Glu Ser Gly Gln Asn Val Thr Ala Arg Asn
145                 150                 155                 160

Phe Pro Pro Ser Gln Asp Ala Ser Gly Asp Leu Tyr Thr Thr Ser Ser
                165                 170                 175

Gln Leu Thr Leu Pro Ala Thr Gln Cys Pro Asp Gly Lys Ser Val Thr
            180                 185                 190

Cys His Val Lys His Tyr Thr Asn Pro Ser Gln Asp Val Thr Val Pro
        195                 200                 205

Cys Pro Val Pro Pro Pro Pro Cys Cys His Pro Arg Leu Ser Leu
    210                 215                 220

His Arg Pro Ala Leu Glu Asp Leu Leu Leu Gly Ser Glu Ala Asn Leu
225                 230                 235                 240
```

```
Thr Cys Thr Leu Thr Gly Leu Arg Asp Ala Ser Gly Ala Thr Phe Thr
                245                 250                 255

Trp Thr Pro Ser Ser Gly Lys Ser Ala Val Gln Gly Pro Pro Glu Arg
            260                 265                 270

Asp Leu Cys Gly Cys Tyr Ser Val Ser Ser Val Leu Pro Gly Cys Ala
        275                 280                 285

Gln Pro Trp Asn His Gly Glu Thr Phe Thr Cys Thr Ala Ala His Pro
    290                 295                 300

Glu Leu Lys Thr Pro Leu Thr Ala Asn Ile Thr Lys Ser Gly Asn Thr
305                 310                 315                 320

Phe Arg Pro Glu Val His Leu Leu Pro Pro Ser Arg Glu Leu Ala
                325                 330                 335

Leu Asn Glu Leu Val Thr Leu Gly Cys Leu Ala Arg Gly Phe Ser Pro
                340                 345                 350

Lys Asp Val Leu Val Arg Trp Leu Gln Gly Ser Gln Glu Leu Pro Arg
            355                 360                 365

Glu Lys Tyr Leu Thr Trp Ala Ser Arg Gln Glu Pro Ser Gln Gly Thr
        370                 375                 380

Thr Thr Phe Ala Val Ile Ser Ile Leu Arg Val Ala Ala Glu Asp Trp
385                 390                 395                 400

Lys Lys Gly Asp Thr Phe Ser Cys Met Val Gly His Glu Ala Leu Pro
                405                 410                 415

Leu Ala Phe Thr Gln Lys Thr Ile Asp Arg Leu Ala Gly Lys Pro Thr
            420                 425                 430

His Val Asn Val Ser Val Val Met Ala Glu Val Asp Gly Thr Cys Tyr
        435                 440                 445

<210> SEQ ID NO 13
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140
```

```
Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
            165                 170                 175

Thr Glu Gln Asp Ser Lys Asp Ser Thr Tyr Ser Leu Ser Ser Thr Leu
        180                 185                 190

Thr Leu Ser Lys Ala Asp Tyr Glu Lys His Lys Val Tyr Ala Cys Glu
    195                 200                 205

Val Thr His Gln Gly Leu Ser Ser Pro Val Thr Lys Ser Phe Asn Arg
210                 215                 220

Gly Glu Cys
225

<210> SEQ ID NO 14
<211> LENGTH: 461
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ser Ser Gly Gly Thr Ser Asn Asn Tyr
            20                  25                  30

Ala Ile Ser Trp Val Arg Gln Ala Pro Gly Gln Gly Leu Asp Trp Met
        35                  40                  45

Gly Gly Ile Ser Pro Ile Phe Gly Ser Thr Ala Tyr Ala Gln Lys Phe
    50                  55                  60

Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

Ala Arg His Gly Asn Tyr Tyr Tyr Ser Gly Met Asp Val Trp Gly
            100                 105                 110

Gln Gly Thr Thr Val Thr Val Ser Ser Ala Ser Pro Thr Ser Pro Lys
        115                 120                 125

Val Phe Pro Leu Ser Leu Asp Ser Thr Pro Gln Asp Gly Asn Val Val
130                 135                 140

Val Ala Cys Leu Val Gln Gly Phe Phe Pro Gln Glu Pro Leu Ser Val
145                 150                 155                 160

Thr Trp Ser Glu Ser Gly Gln Asn Val Thr Ala Arg Asn Phe Pro Pro
            165                 170                 175

Ser Gln Asp Ala Ser Gly Asp Leu Tyr Thr Thr Ser Ser Gln Leu Thr
        180                 185                 190

Leu Pro Ala Thr Gln Cys Pro Asp Gly Lys Ser Val Thr Cys His Val
    195                 200                 205

Lys His Tyr Thr Asn Pro Ser Gln Asp Val Thr Val Pro Cys Pro Val
210                 215                 220

Pro Pro Pro Pro Pro Cys Cys His Pro Arg Leu Ser Leu His Arg Pro
225                 230                 235                 240

Ala Leu Glu Asp Leu Leu Leu Gly Ser Glu Ala Asn Leu Thr Cys Thr
            245                 250                 255

Leu Thr Gly Leu Arg Asp Ala Ser Gly Ala Thr Phe Thr Trp Thr Pro
```

```
                260                 265                 270
Ser Ser Gly Lys Ser Ala Val Gln Gly Pro Pro Glu Arg Asp Leu Cys
            275                 280                 285

Gly Cys Tyr Ser Val Ser Val Leu Pro Gly Cys Ala Gln Pro Trp
        290                 295                 300

Asn His Gly Glu Thr Phe Thr Cys Thr Ala Ala His Pro Glu Leu Lys
305                 310                 315                 320

Thr Pro Leu Thr Ala Asn Ile Thr Lys Ser Gly Asn Thr Phe Arg Pro
                325                 330                 335

Glu Val Glu Leu Met Pro Pro Ser Glu Glu Leu Ala Leu Asn Glu
            340                 345                 350

Leu Val Thr Leu Trp Cys Leu Ala Arg Gly Phe Ser Pro Lys Asp Val
            355                 360                 365

Leu Val Arg Trp Leu Gln Gly Ser Gln Glu Leu Pro Arg Glu Lys Tyr
            370                 375                 380

Leu Thr Trp Ala Ser Arg Gln Glu Pro Ser Gln Gly Thr Thr Thr Phe
385                 390                 395                 400

Ala Val Thr Ser Ile Leu Arg Val Ala Ala Glu Asp Trp Lys Lys Gly
                405                 410                 415

Asp Thr Phe Ser Cys Met Val Gly His Glu Ala Leu Pro Leu Ala Phe
                420                 425                 430

Thr Gln Lys Thr Ile Asp Arg Leu Ala Gly Lys Pro Thr His Val Asn
            435                 440                 445

Val Ser Val Val Met Ala Glu Val Asp Gly Thr Cys Tyr
450                 455                 460

<210> SEQ ID NO 15
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ser Tyr Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
                20                  25                  30

Ser Val Asn Trp Tyr Gln Gln Phe Pro Gly Thr Ala Pro Lys Leu Leu
            35                  40                  45

Ile Tyr Ser Asn Asp Gln Arg Pro Ser Val Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Ser Leu
                85                  90                  95

Lys Gly Ala Val Phe Gly Gly Gly Thr Gln Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 16
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Asp Tyr Thr Leu Thr Ile Thr Ser Leu Gln Ser
65                  70                  75                  80

Glu Asp Phe Ala Val Tyr Tyr Cys Gln His Tyr Ser Asn Trp Pro Pro
                85                  90                  95

Arg Leu Thr Phe Gly Gly Gly Thr Lys Val Glu Ile Lys Ser Ser Ala
            100                 105                 110

Ser Pro Thr Ser Pro Lys Val Phe Pro Leu Ser Leu Asp Ser Thr Pro
            115                 120                 125

Gln Asp Gly Asn Val Val Val Ala Cys Leu Val Gln Gly Phe Phe Pro
        130                 135                 140

Gln Glu Pro Leu Ser Val Thr Trp Ser Glu Ser Gly Gln Asn Val Thr
145                 150                 155                 160

Ala Arg Asn Phe Pro Pro Ser Gln Asp Ala Ser Gly Asp Leu Tyr Thr
            165                 170                 175

Thr Ser Ser Gln Leu Thr Leu Pro Ala Thr Gln Cys Pro Asp Gly Lys
            180                 185                 190

Ser Val Thr Cys His Val Lys His Tyr Thr Asn Pro Ser Gln Asp Val
            195                 200                 205

Thr Val Pro Cys Pro Val Pro Pro Pro Pro Cys Cys His Pro Arg
            210                 215                 220

Leu Ser Leu His Arg Pro Ala Leu Glu Asp Leu Leu Leu Gly Ser Glu
225                 230                 235                 240

Ala Asn Leu Thr Cys Thr Leu Thr Gly Leu Arg Asp Ala Ser Gly Ala
            245                 250                 255

Thr Phe Thr Trp Thr Pro Ser Ser Gly Lys Ser Ala Val Gln Gly Pro
            260                 265                 270

Pro Glu Arg Asp Leu Cys Gly Cys Tyr Ser Val Ser Ser Val Leu Pro
            275                 280                 285
```

```
Gly Cys Ala Gln Pro Trp Asn His Gly Glu Thr Phe Thr Cys Thr Ala
    290                 295                 300

Ala His Pro Glu Leu Lys Thr Pro Leu Thr Ala Asn Ile Thr Lys Ser
305                 310                 315                 320

Gly Asn Thr Phe Arg Pro Glu Val His Leu Leu Pro Pro Ser Arg
                325                 330                 335

Glu Leu Ala Leu Asn Glu Leu Val Thr Leu Gly Cys Leu Ala Arg Gly
                340                 345                 350

Phe Ser Pro Lys Asp Val Leu Val Arg Trp Leu Gln Gly Ser Gln Glu
                355                 360                 365

Leu Pro Arg Glu Lys Tyr Leu Thr Trp Ala Ser Arg Gln Glu Pro Ser
370                 375                 380

Gln Gly Thr Thr Thr Phe Ala Val Ile Ser Ile Leu Arg Val Ala Ala
385                 390                 395                 400

Glu Asp Trp Lys Lys Gly Asp Thr Phe Ser Cys Met Val Gly His Glu
                405                 410                 415

Ala Leu Pro Leu Ala Phe Thr Gln Lys Thr Ile Asp Arg Leu Ala Gly
                420                 425                 430

Lys Pro Thr His Val Asn Val Ser Val Val Met Ala Glu Val Asp Gly
                435                 440                 445

Thr Cys Tyr
    450

<210> SEQ ID NO 17
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Val Gln Leu Val Glu Ser Gly Gly Gly Val Val Gln Pro Gly Lys
1               5                   10                  15

Ser Leu Arg Leu Ser Cys Ala Ala Ser Gly Leu Thr Phe Ser Ser Tyr
            20                  25                  30

Ala Val His Trp Val Arg Gln Ala Pro Gly Lys Gly Leu Glu Trp Val
        35                  40                  45

Thr Leu Ile Ser Tyr Asp Gly Ala Asn Gln Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Val Pro Gly Pro Val Phe Gly Ile Phe Pro Pro Trp Ser Tyr Phe
            100                 105                 110

Asp Asn Trp Gly Gln Gly Ile Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
```

```
                    180                 185                 190
Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 18
<211> LENGTH: 462
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asn Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Glu Asp Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Trp Gly Met Val Arg Gly Val Ile Asp Val Phe Asp Ile Trp
        100                 105                 110

Gly Gln Gly Thr Val Val Thr Val Ser Ser Ala Ser Pro Thr Ser Pro
    115                 120                 125

Lys Val Phe Pro Leu Ser Leu Asp Ser Thr Pro Gln Asp Gly Asn Val
130                 135                 140

Val Val Ala Cys Leu Val Gln Gly Phe Phe Pro Gln Glu Pro Leu Ser
145                 150                 155                 160

Val Thr Trp Ser Glu Ser Gly Gln Asn Val Thr Ala Arg Asn Phe Pro
            165                 170                 175

Pro Ser Gln Asp Ala Ser Gly Asp Leu Tyr Thr Thr Ser Ser Gln Leu
        180                 185                 190

Thr Leu Pro Ala Thr Gln Cys Pro Asp Gly Lys Ser Val Thr Cys His
    195                 200                 205

Val Lys His Tyr Thr Asn Pro Ser Gln Asp Val Thr Val Pro Cys Pro
    210                 215                 220

Val Pro Pro Pro Pro Cys Cys His Pro Arg Leu Ser Leu His Arg
225                 230                 235                 240

Pro Ala Leu Glu Asp Leu Leu Leu Gly Ser Glu Ala Asn Leu Thr Cys
            245                 250                 255

Thr Leu Thr Gly Leu Arg Asp Ala Ser Gly Ala Thr Phe Thr Trp Thr
        260                 265                 270

Pro Ser Ser Gly Lys Ser Ala Val Gln Gly Pro Pro Glu Arg Asp Leu
    275                 280                 285

Cys Gly Cys Tyr Ser Val Ser Ser Val Leu Pro Gly Cys Ala Gln Pro
        290                 295                 300
```

```
Trp Asn His Gly Glu Thr Phe Thr Cys Thr Ala Ala His Pro Glu Leu
305                 310                 315                 320

Lys Thr Pro Leu Thr Ala Asn Ile Thr Lys Ser Gly Asn Thr Phe Arg
                325                 330                 335

Pro Glu Val Glu Leu Met Pro Pro Ser Glu Glu Leu Ala Leu Asn
            340                 345                 350

Glu Leu Val Thr Leu Trp Cys Leu Ala Arg Gly Phe Ser Pro Lys Asp
                355                 360                 365

Val Leu Val Arg Trp Leu Gln Gly Ser Gln Glu Leu Pro Arg Glu Lys
        370                 375                 380

Tyr Leu Thr Trp Ala Ser Arg Gln Glu Pro Ser Gln Gly Thr Thr Thr
385                 390                 395                 400

Phe Ala Val Thr Ser Ile Leu Arg Val Ala Ala Glu Asp Trp Lys Lys
                405                 410                 415

Gly Asp Thr Phe Ser Cys Met Val Gly His Glu Ala Leu Pro Leu Ala
                420                 425                 430

Phe Thr Gln Lys Thr Ile Asp Arg Leu Ala Gly Lys Pro Thr His Val
                435                 440                 445

Asn Val Ser Val Val Met Ala Glu Val Asp Gly Thr Cys Tyr
450                 455                 460

<210> SEQ ID NO 19
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Ile Gln Met Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 20
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Thr
                85                  90                  95

Trp Thr Phe Gly Gln Gly Thr Lys Val Glu Ile Lys Ser Ser Ala Ser
            100                 105                 110

Pro Thr Ser Pro Lys Val Phe Pro Leu Ser Leu Asp Ser Thr Pro Gln
        115                 120                 125

Asp Gly Asn Val Val Val Ala Cys Leu Val Gln Gly Phe Phe Pro Gln
130                 135                 140

Glu Pro Leu Ser Val Thr Trp Ser Glu Ser Gly Gln Asn Val Thr Ala
145                 150                 155                 160

Arg Asn Phe Pro Pro Ser Gln Asp Ala Ser Gly Asp Leu Tyr Thr Thr
                165                 170                 175

Ser Ser Gln Leu Thr Leu Pro Ala Thr Gln Cys Pro Asp Gly Lys Ser
            180                 185                 190

Val Thr Cys His Val Lys His Tyr Thr Asn Pro Ser Gln Asp Val Thr
        195                 200                 205

Val Pro Cys Pro Val Pro Pro Pro Pro Cys Cys His Pro Arg Leu
210                 215                 220

Ser Leu His Arg Pro Ala Leu Glu Asp Leu Leu Leu Gly Ser Glu Ala
225                 230                 235                 240

Asn Leu Thr Cys Thr Leu Thr Gly Leu Arg Asp Ala Ser Gly Ala Thr
                245                 250                 255

Phe Thr Trp Thr Pro Ser Ser Gly Lys Ser Ala Val Gln Gly Pro Pro
            260                 265                 270

Glu Arg Asp Leu Cys Gly Cys Tyr Ser Val Ser Ser Val Leu Pro Gly
        275                 280                 285

Cys Ala Gln Pro Trp Asn His Gly Glu Thr Phe Thr Cys Thr Ala Ala
    290                 295                 300

His Pro Glu Leu Lys Thr Pro Leu Thr Ala Asn Ile Thr Lys Ser Gly
305                 310                 315                 320

Asn Thr Phe Arg Pro Glu Val His Leu Leu Pro Pro Pro Ser Arg Glu 325                 330                 335
Leu Ala Leu Asn Glu Leu Val Thr Leu Gly Cys Leu Ala Arg Gly Phe
            340                 345                 350

Ser Pro Lys Asp Val Leu Val Arg Trp Leu Gln Gly Ser Gln Glu Leu
            355                 360                 365

Pro Arg Glu Lys Tyr Leu Thr Trp Ala Ser Arg Gln Glu Pro Ser Gln
        370                 375                 380

Gly Thr Thr Thr Phe Ala Val Ile Ser Ile Leu Arg Val Ala Ala Glu
385                 390                 395                 400

Asp Trp Lys Lys Gly Asp Thr Phe Ser Cys Met Val Gly His Glu Ala
                405                 410                 415

Leu Pro Leu Ala Phe Thr Gln Lys Thr Ile Asp Arg Leu Ala Gly Lys
            420                 425                 430

Pro Thr His Val Asn Val Ser Val Val Met Ala Glu Val Asp Gly Thr
        435                 440                 445

Cys Tyr
    450

<210> SEQ ID NO 21
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Val Gln Leu Val Gln Ser Gly Ala Glu Val Lys Lys Ser Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Phe Tyr Pro Gly Asp Ser Ser Thr Arg Tyr Ser Pro Ser Phe
    50                  55                  60

Gln Gly Gln Val Thr Ile Ser Ala Asp Lys Ser Val Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Arg Asn Trp Gly Asn Ala Phe Asp Ile Trp Gly Gln Gly
            100                 105                 110

Thr Met Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225

<210> SEQ ID NO 22
<211> LENGTH: 329
<212> TYPE: PRT
<213> ORGANISM: Homo sapiens

<400> SEQUENCE: 22

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 23
<211> LENGTH: 472
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Pro Thr Ser Pro Lys Val Phe
        115                 120                 125

Pro Leu Ser Leu Cys Ser Thr Gln Pro Asp Gly Asn Val Val Ile Ala
    130                 135                 140

Cys Leu Val Gln Gly Phe Phe Pro Gln Glu Pro Leu Ser Val Thr Trp
145                 150                 155                 160

Ser Glu Ser Gly Gln Gly Val Thr Ala Arg Asn Phe Pro Pro Ser Gln
                165                 170                 175

Asp Ala Ser Gly Asp Leu Tyr Thr Thr Ser Ser Gln Leu Thr Leu Pro
            180                 185                 190

Ala Thr Gln Cys Leu Ala Gly Lys Ser Val Thr Cys His Val Lys His
        195                 200                 205

Tyr Thr Asn Pro Ser Gln Asp Val Thr Val Pro Cys Pro Val Pro Ser
    210                 215                 220

Thr Pro Pro Thr Pro Ser Pro Ser Thr Pro Pro Thr Pro Ser Pro Ser
225                 230                 235                 240

Cys Cys His Pro Arg Leu Ser Leu His Arg Pro Ala Leu Glu Asp Leu
                245                 250                 255

Leu Leu Gly Ser Glu Ala Asn Leu Thr Cys Thr Leu Thr Gly Leu Arg
            260                 265                 270

Asp Ala Ser Gly Val Thr Phe Thr Trp Thr Pro Ser Ser Gly Lys Ser
        275                 280                 285

Ala Val Gln Gly Pro Pro Glu Arg Asp Leu Cys Gly Cys Tyr Ser Val
    290                 295                 300

Ser Ser Val Leu Pro Gly Cys Ala Glu Pro Trp Asn His Gly Lys Thr
305                 310                 315                 320

Phe Thr Cys Thr Ala Ala Tyr Pro Glu Ser Lys Thr Pro Leu Thr Ala
                325                 330                 335

Thr Leu Ser Lys Ser Gly Asn Thr Phe Arg Pro Glu Val His Leu Leu
            340                 345                 350

Pro Pro Pro Ser Glu Glu Leu Ala Leu Asn Glu Leu Val Thr Leu Thr
        355                 360                 365

Cys Leu Ala Arg Gly Phe Ser Pro Lys Asp Val Leu Val Arg Trp Leu
    370                 375                 380
```

Gln Gly Ser Gln Glu Leu Pro Arg Glu Lys Tyr Leu Thr Trp Ala Ser
385                 390                 395                 400

Arg Gln Glu Pro Ser Gln Gly Thr Thr Thr Phe Ala Val Thr Ser Ile
                405                 410                 415

Leu Arg Val Ala Ala Glu Asp Trp Lys Lys Gly Asp Thr Phe Ser Cys
            420                 425                 430

Met Val Gly His Glu Ala Leu Pro Leu Ala Phe Thr Gln Lys Thr Ile
        435                 440                 445

Asp Arg Leu Ala Gly Lys Pro Thr His Val Asn Val Ser Val Val Met
    450                 455                 460

Ala Glu Val Asp Gly Thr Cys Tyr
465                 470

<210> SEQ ID NO 24
<211> LENGTH: 264
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gly Glu Gln Lys Leu Ile Ser Glu Glu Asp Leu Gly Gly Gly Gly Ser
1               5                   10                  15

Thr Pro Pro Thr Pro Ser Pro Ser Thr Pro Pro Thr Pro Ser Pro Ser
                20                  25                  30

Cys Cys His Pro Arg Leu Ser Leu His Arg Pro Ala Leu Glu Asp Leu
            35                  40                  45

Leu Leu Gly Ser Glu Ala Asn Leu Thr Cys Thr Leu Thr Gly Leu Arg
50                  55                  60

Asp Ala Ser Gly Val Thr Phe Thr Trp Thr Pro Ser Ser Gly Lys Ser
65                  70                  75                  80

Ala Val Gln Gly Pro Pro Glu Arg Asp Leu Cys Gly Cys Tyr Ser Val
                85                  90                  95

Ser Ser Val Leu Pro Gly Cys Ala Glu Pro Trp Asn His Gly Lys Thr
            100                 105                 110

Phe Thr Cys Thr Ala Ala Tyr Pro Glu Ser Lys Thr Pro Leu Thr Ala
        115                 120                 125

Thr Leu Ser Lys Ser Gly Asn Thr Phe Arg Pro Glu Val His Leu Leu
    130                 135                 140

Pro Pro Pro Ser Glu Glu Leu Ala Leu Asn Glu Leu Val Thr Leu Thr
145                 150                 155                 160

Cys Leu Ala Arg Gly Phe Ser Pro Lys Asp Val Leu Val Arg Trp Leu
                165                 170                 175

Gln Gly Ser Gln Glu Leu Pro Arg Glu Lys Tyr Leu Thr Trp Ala Ser
            180                 185                 190

Arg Gln Glu Pro Ser Gln Gly Thr Thr Thr Phe Ala Val Thr Ser Ile
        195                 200                 205

Leu Arg Val Ala Ala Glu Asp Trp Lys Lys Gly Asp Thr Phe Ser Cys
    210                 215                 220

Met Val Gly His Glu Ala Leu Pro Leu Ala Phe Thr Gln Lys Thr Ile
225                 230                 235                 240

Asp Arg Leu Ala Gly Lys Pro Thr His Val Asn Val Ser Val Val Met
                245                 250                 255

Ala Glu Val Asp Gly Thr Cys Tyr
            260

<210> SEQ ID NO 25
<211> LENGTH: 479
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Pro Val Pro Ser Thr Pro Thr Pro Ser Pro Ser Thr
225                 230                 235                 240

Pro Pro Thr Pro Ser Pro Ser Cys Cys His Pro Arg Leu Ser Leu His
                245                 250                 255

Arg Pro Ala Leu Glu Asp Leu Leu Gly Ser Glu Ala Asn Leu Thr
            260                 265                 270

Cys Thr Leu Thr Gly Leu Arg Asp Ala Ser Gly Val Thr Phe Thr Trp
        275                 280                 285

Thr Pro Ser Ser Gly Lys Ser Ala Val Gln Gly Pro Pro Glu Arg Asp
    290                 295                 300

Leu Cys Gly Cys Tyr Ser Val Ser Ser Val Leu Pro Gly Cys Ala Glu
305                 310                 315                 320

Pro Trp Asn His Gly Lys Thr Phe Thr Cys Thr Ala Ala Tyr Pro Glu
                325                 330                 335

Ser Lys Thr Pro Leu Thr Ala Thr Leu Ser Lys Ser Gly Asn Thr Phe

```
                    340                 345                 350
Arg Pro Glu Val His Leu Leu Pro Pro Ser Glu Glu Leu Ala Leu
            355                 360                 365

Asn Glu Leu Val Thr Leu Thr Cys Leu Ala Arg Gly Phe Ser Pro Lys
    370                 375                 380

Asp Val Leu Val Arg Trp Leu Gln Gly Ser Gln Glu Leu Pro Arg Glu
385                 390                 395                 400

Lys Tyr Leu Thr Trp Ala Ser Arg Gln Glu Pro Ser Gln Gly Thr Thr
                405                 410                 415

Thr Phe Ala Val Thr Ser Ile Leu Arg Val Ala Ala Glu Asp Trp Lys
            420                 425                 430

Lys Gly Asp Thr Phe Ser Cys Met Val Gly His Glu Ala Leu Pro Leu
        435                 440                 445

Ala Phe Thr Gln Lys Thr Ile Asp Arg Leu Ala Gly Lys Pro Thr His
    450                 455                 460

Val Asn Val Ser Val Val Met Ala Glu Val Asp Gly Thr Cys Tyr
465                 470                 475

<210> SEQ ID NO 26
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Val Ala Ala Pro
            100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 27
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ser Ser Ala Ser Thr Lys
            100                 105                 110

Gly Pro Ser Val Phe Pro Leu Ala Pro Ser Ser Lys Ser Thr Ser Gly
        115                 120                 125

Gly Thr Ala Ala Leu Gly Cys Leu Val Lys Asp Tyr Phe Pro Glu Pro
    130                 135                 140

Val Thr Val Ser Trp Asn Ser Gly Ala Leu Thr Ser Gly Val His Thr
145                 150                 155                 160

Phe Pro Ala Val Leu Gln Ser Ser Gly Leu Tyr Ser Leu Ser Ser Val
                165                 170                 175

Val Thr Val Pro Ser Ser Ser Leu Gly Thr Gln Thr Tyr Ile Cys Asn
            180                 185                 190

Val Asn His Lys Pro Ser Asn Thr Lys Val Asp Lys Arg Val Glu Pro
        195                 200                 205

Lys Ser Cys
    210
```

IGA MULTI-SPECIFIC BINDING MOLECULES

CROSS-REFERENCE TO RELATED APPLICATIONS

This application is a U.S. national stage entry, filed under 35 U.S.C. § 371, of PCT Application No. PCT/US2015/015268, filed on Feb. 10, 2015, which claims the benefit of priority under 35 U.S.C. § 119(e) of U.S. Provisional Pat. Application Ser. No. 61/937,984, filed Feb. 10, 2014, the entire contents of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Feb. 10, 2015, is named IGM-0003PCT_SL.txt and is 73,879 bytes in size.

FIELD OF THE INVENTION

The present invention concerns IgA multi-specific binding molecules. In particular, the invention concerns multi-specific, including bi-specific, binding molecules comprising IgA heavy chain sequences, and methods for their preparation and use.

BACKGROUND OF THE INVENTION

Since the advent of humanized antibodies, the therapeutic use of antibodies such as Rituxan® (rituximab), Herceptin® (trastuzumab) and Avastin® (bevacizumab), has revolutionized the fields of medicine, including oncology, the treatment of inflammatory disorders, such as rheumatoid arthritis, and many other indications. In the United States, more than 30 human or humanized antibodies have been approved for clinical use, and more than 600 new antibodies or antibody-like molecules are in various stages of development. Some antibodies have antagonistic function on soluble target molecules such as vascular endothelial growth factor (VEGF) or tumor necrosis factor (TNF), whose actions are part of the pathologic process of a disease. Alternatively, antibodies can bind, block and/or induce destruction of pathologic cells in certain diseases, such as cancer. The main functions of these therapeutic antibodies are binding through the Fab region, and recruitment of effector function via the Fc domain (which also mediates the long circulating half-life of antibodies). One of the major advantages of antibodies compared to small molecule drugs, can be their exquisite specificity. Antibodies can very accurately target selected protein antigens, such as oncogene products, to the exclusion of very similar homologs, allowing for benign safety profiles. Hence, antibodies are well characterized for specific single targeting function.

As the field has progressed, antibody function has been enhanced through creative means of protein engineering, such as to provide higher affinity, longer half-life, and/or better tissue distribution, as well as combination of small and large molecule technologies for increased focus of cell destruction via toxic payload delivery (e.g. antibody-drug conjugates). Another approach to improving antibody function takes advantage of the bivalent binding of the immunoglobulin G (IgG) structure which allows one IgG molecule to bind two antigens. Indeed, in certain applications, there exists good potential for asymmetric antibodies to exert useful functions by simultaneously binding two different target antigens. To address this need, a variety of constructs have been produced to yield a single molecule that can bind two different antigens, allowing for functions never before seen in nature. An example of this bi-specific approach is "blinatumumab" (MT103) which binds the CD3 and CD19 receptors, on T- and B-cells, respectively. This tethering of a cytotoxic T cell to a cancerous B-cell allows for effective treatment of B-cell leukemia.

However, there remain significant technical difficulties in construction, expression and production of bispecific antibodies. Although bispecific antibodies are regarded as promising therapeutic agents due to their ability to simultaneously bind two different antigens, their utility is limited due to problems with stability and manufacturing complexity.

Various forms of protein engineering have been used to match heterologous heavy chains, plus appropriate pairwise matching of heavy and light chains to efficiently yield a bi-specific IgG. In addition, various bispecific antibody formats, including quadromas, chemical heteroconjugates, recombinant constructs using selected heterodimerization domains and recombinant constructs of minimal size consisting of two minimal antigen-binding sites.

However, all of these efforts have been fraught with difficulty.

Thus, despite efforts directed toward the development of bispecific therapeutic antibodies, there remains a great need for developing more efficient platforms that can lead to more efficient and flexible production of bi- and multispecific antibodies, thereby shortening the timeline between discovery and clinical introduction of such therapeutics and enabling the design and production of new types of antibody formats with multiple specificities and/or valencies.

This is particularly true for IgA antibodies, in view of the involvement of IgA in the body's first specific immunologic defense against infection, including bacterial and viral infections, and contribution of dimeric IgA antibodies to the humoral part of the mucosal immune system. Bi- and multi-specific IgA antibodies have therefore great potential in the treatment of respiratory virus infections, various bacterial infections of the gastrointestinal tract, and immunotherapy of cancer. Thus, bispecific IgA antibodies to respiratory syncytial virus (RSV) antigens find utility in the treatment of RSV infection of the lung, bispecific IgA antibodies to influenza virus antigens are effective in the treatment of flu, and bispecific IgA antibodies to *Clostridium difficile* (*C. difficile*) Toxins A and B are useful in treating *C. difficile* infection, responsible for most of infectious diarrhea in hospital patients.

SUMMARY OF THE INVENTION

In one aspect, the invention concerns a multi-specific binding molecule comprising two binding units and at least two binding specificities, wherein each of the binding units comprises two IgA heavy chain constant region sequences conjugated to a binding region to a binding target.

In one embodiment, the multi-specific binding molecule is bispecific. In a particular embodiment, in a bispecific binding molecule each of the binding units is monospecific (AA, BB), each binding to a different binding target (A and B, respectively). In another embodiment, in a bispecific binding molecule one of the two binding units is monospecific (AA) and the other binding unit is bispecific, wherein one of the binding specificities of the bispecific binding unit is the same as the binding specificity of the monospecific binding unit (AB). In yet another embodiment, in a bispecific binding molecule each of the binding units is bispecific, each having the same two binding specificities (AB, AB). In a further embodiment, in a bispecific binding molecule, each of the binding units is bispecific, and the binding molecule has three binding specificities (AB, AC). In a still further embodiment, in a bispecific binding molecule, each of the binding units is bispecific, and the binding molecule has four binding specificities (AB, CD).

In a specific embodiment, the multi-specific binding molecule is an IgA antibody, wherein the binding region sequences comprise IgA heavy chain variable region sequences.

In a further embodiment, the IgA antibody comprises two IgA binding units, each comprising an IgA heavy chain constant region sequence fused to an IgA heavy chain variable region sequence, optionally further comprising an IgA J region.

In another embodiment, the IgA heavy chain constant region sequences comprise at least a CA3 domain.

In yet another embodiment, the multi-specific binding molecule, e.g. a bispecific IgA antibody, further comprises at least one IgA light chain variable region sequence associated with the IgA heavy chain variable region sequence in at least one of the two binding units, preferably in each of the two binding units.

In one embodiment, if at least one of the two binding units is bispecific, an asymmetric interface is created between two different IgA heavy chain constant regions, e.g. by knobs-into-holes coupling and/or salt bridges coupling, such as by one or more modifications set forth in Tables 1 and 2.

In a further embodiment, in a multi-specific (e.g. bispecific) IgA antibody comprising at least one light chain variable region, the light chain variable region sequence is coupled to its matching heavy chain variable region by creating an asymmetric interface between the light and heavy chains, e.g. using one or more of CrossMab technique, knobs-into-holes coupling and salt bridges coupling.

In all embodiments of the present invention, the multi-specific binding molecule of may be conjugated to a toxin and/or to a chemotherapeutic agent, wherein the conjugation may be by fusion and/or by a chemical linker.

In all embodiments of the present invention, the multi-specific IgA antibody may be chimeric or humanized or human.

In another aspect, the invention concerns a composition comprising at least about 70% of a multi-specific binding molecule of the present invention.

In further specific embodiments, the invention concerns a dimeric bispecific IgA binding molecule wherein each of the binding units is monospecific (AA, BB), each binding to a different binding target (A and B, respectively). In another embodiment, one of the two binding units is monospecific (AA) and the other binding unit is bispecific, wherein one of the binding specificities of the bispecific binding unit is the same as the binding specificity of the monospecific binding unit (AB). In a further embodiment, each of the binding units is bispecific, each having the same two binding specificities (AB, AB). In a still further embodiment, each of the binding units is bispecific, and the binding molecule has three binding specificities (AB, AC). In yet another embodiment, each of the binding units is bispecific, and the binding molecule has four binding specificities (AB, CD). In all embodiments, the binding molecule preferably is a dimeric bispecific IgA (IgA1 or IgA2) antibody, preferably comprising a light chain, and preferably comprising a J chain.

In a specific embodiment, the multi-specific binding molecule comprises two IgA binding units in end-to-end configuration, each comprising an IgA heavy chain constant region sequence fused to an IgA heavy chain variable region sequence, optionally further comprising an IgA J region, e.g. a J region comprising the sequence of SEQ ID NO: 3.

In all embodiments, the IgA heavy chain constant region sequences preferably comprise at least a CA3 domain.

In all embodiments, the multi-specific binding molecules herein further comprise at least one IgA light chain variable region sequence associated with the IgA heavy chain variable region sequence in at least one of the two binding units.

In another embodiment, at least one of the binding units is bispecific, and wherein an asymmetric interface is created between two different IgA heavy chain constant regions. In all embodiments, the asymmetric interface may be created by knobs-into-holes coupling and/or salt bridges coupling, such as using one or more modifications set forth in Tables 1 and 2.

In all embodiments, in the multi-specific binding molecule the light chain variable region sequence, if present, may be coupled to its matching heavy chain variable region by creating an asymmetric interface between the light and heavy chains. In all embodiments, the asymmetric interface may be created by CrossMab technique, knobs-into-holes coupling and/or salt bridges coupling.

In various further embodiments, the multi-specific binding molecule may be conjugated to a toxin or a chemotherapeutic agent, wherein conjugation might, for example, be achieved by covalent linkage, e.g. by fusion or by a chemical linker.

In all embodiments, the multi-specific, e.g. bispecific IgA antibodies of the invention might be chimeric or humanized.

In a further embodiment, the invention concerns a multi-specific dimeric IgA antibody specifically binding to different antigens of a respiratory syncytial virus (RSV). The antibody preferably is bispecific, and comprises two binding moieties for RSV F and two binding moieties for RSV G. In a specific embodiment, the binding moiety for RSV G comprises a heavy chain variable region sequence of SEQ ID NO: 10 and a light chain variable region of SEQ ID NO: 11. In another specific embodiment, the binding moiety for RSV F comprises a heavy chain variable region sequence of SEQ ID NO: 12 and a light chain variable region sequence of SEQ ID NO: 13.

In a further embodiment, the invention concerns a multi-specific dimeric IgA antibody specifically binding to different influenza A virus antigens. The antibody preferably is bispecific comprising two binding moieties to each influenza A virus antigen. In a specific embodiment, the binding moiety to a first influenza A virus antigen comprises a heavy chain variable region sequence of SEQ ID NO: 14 and a light chain variable region sequence of SEQ ID NO: 15. In another specific embodiment, the binding moiety to a second influenza A virus antigen comprises a first variable region sequence of SEQ ID NO: 16. In yet another specific embodiment, the binding moiety to the second influenza A virus antigen comprises a second variable region sequence of SEQ ID NO: 17.

In a further embodiment, the invention concerns a multi-specific dimeric IgA antibody specifically binding to different antigens of *Clostridium difficile* (*C. difficile*). The antibody preferably is bispecific. In a preferred embodiment, the antibody comprises two binding moieties for Toxin A and two binding moieties for Toxin B of *C. difficile*. In a specific embodiment, the binding moiety to Toxin A comprises a heavy chain variable region sequence of SEQ ID NO: 18. In another specific embodiment, the binding moiety to Toxin A comprises a light chain variable region sequence of SEQ ID NO: 19. In a further specific embodiment, the binding moiety to Toxin B comprises a first variable region sequence of SEQ ID NO: 20. In yet another specific embodiment, the binding moiety to Toxin B comprises a second variable region sequence of SEQ ID NO: 21.

In another aspect, the invention concerns a composition comprising at least about 70% of any of the multi-specific IgA binding molecules herein.

In a further aspect, the invention concerns a pharmaceutical composition comprising an effective amount of any of the multi-specific IgA binding molecules herein. In various embodiments, the pharmaceutical compositions may be for the treatment of a microbial infection, including bacteria, viral and fungal infections, such as for example, *C. difficile* infection, a respiratory virus infection, e.g. an influenza virus infection or a respiratory syncytial virus (RSV) infection.

In a still further aspect, the invention concerns method of treatment and uses for the preparation of pharmaceutical compositions to treat microbial infections, including bacteria, viral and fungal infections, specifically including any and all infections listed above and throughout the disclosure.

BRIEF DESCRIPTION OF THE DRAWINGS

FIGS. 2A, 2B and 2C shows the alignment of IgG1 and IgA1 and IgA2 heavy chain constant regions. The human IgG1 heavy chain constant region sequence is from J00228 (Takahashi et al., Cell 29:671-679 (1982); SEQ ID NO: 22); the human IgA1 heavy chain constant region sequence (UniProt P01876-IGHA1-HUMAN; SEQ ID NO: 1) and numbering is from PDB 2QEJ (Ramsland et al., Proc Natl Acad Sci USA 104:15051-15056 (2007)) and from IgA BUR (Putnam et al., J Biol Chem 254:2865-2874 (1979)); and the human IgA2 heavy chain constant region sequence numbering corresponds to UniProt P01877-IGHA2_HUMAN (SEQ ID NO: 2).

FIG. 2A shows the alignment of human IgG1 (SEQ ID NO: 22), IgA1 (SEQ ID NO: 1), and IgA2 (SEQ ID NO: 2) Fc CG1/CA1 heavy chain constant domains as part of the heavy chain constant region sequence.

FIG. 2B shows the alignment of human IgG1 (SEQ ID NO: 22), IgA1 (SEQ ID NO: 1), and IgA2 (SEQ ID NO: 2), IgA1 and IgA2 Fc CG2/CA2 heavy chain constant domains as part of the heavy chain constant region sequence.

FIG. 2C shows the alignment of human IgG1 (SEQ ID NO: 22 ), IgA1 (SEQ ID NO: 1), and IgA2 (SEQ ID NO: 2), IgA1 and IgA2 Fc CG3/CA3 heavy chain constant domains as part of the heavy chain constant region sequence.

Figure 1:
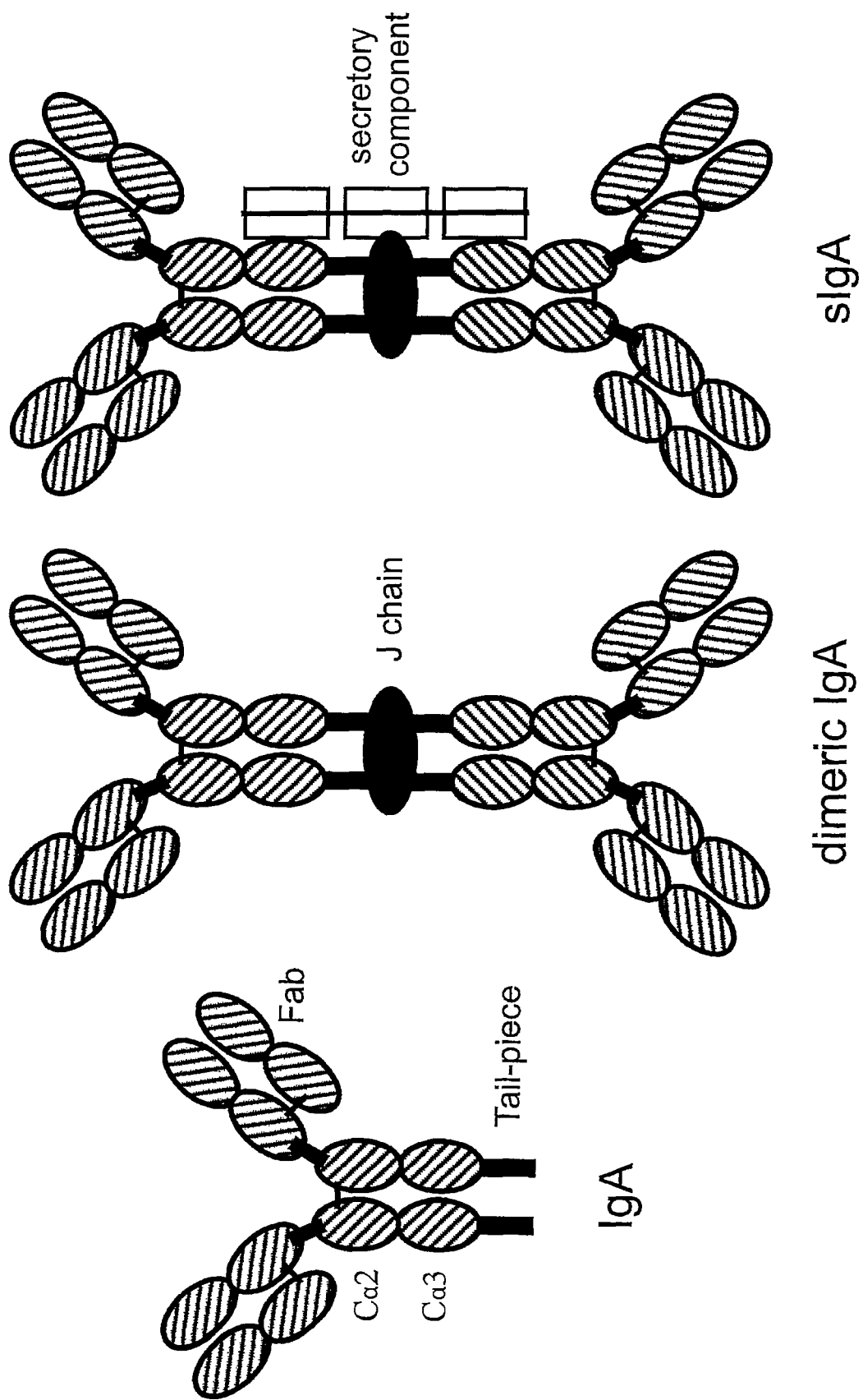
FIG. 1 shows the schematic structures of IgA, dimeric IgA, and secretory IgA (sIgA).

Table 1 shows the IgA CA3 domain interface residues in knobs-holes and charge introduction positions. The sequence of human IgA2 with a Set #1, Knob, CA3 #1 mutation is shown as SEQ ID NO: 4: and the sequence of human IgA2 with a Se #1, Hole, CA3 #2 mutation is shown as SEQ ID NO: 5.

TABLE 1

Human IgA CA3 Domain Interface Residues Knobs-Holes and charge Introduction Positions

| Residue # (FIG. 2, Bur) | IgA1 (SEQ ID NO: 1) | IgA2 (SEQ ID NO: 2) | Native Seq | Potential Mutations |
|---|---|---|---|---|
| Set #1 ||||| 
| Knob (CA3 #1) ||||| 
| 352 | 233 | 220 | L | L,M |
| 368 | 249 | 236 | T | W |
| Hole (CA3 #2): any Combination ||||| 
| 352 | 233 | 220 | L | L,K (R,W) |
| 368 | 249 | 236 | T | G |
| 414 | 295 | 282 | T | I (V, L) |
| Set #2 ||||| 
| Knob (CA3 #1) ||||| 
| 352 | 233 | 220 | L | L,M (H,F,Y) |
| 368 | 249 | 236 | T | F |
| 414 | 295 | 282 | T | G |
| Hole (CA3 #2): any Combination ||||| 
| 352 | 233 | 220 | L | L,K (R,W) |
| 368 | 249 | 236 | T | V (I) |
| 414 | 295 | 282 | T | V (I) |
| Set #3 ||||| 
| Knob (CA3 #1) ||||| 
| 352 | 233 | 220 | L | L,M |
| 368 | 249 | 236 | T | Y |
| 414 | 295 | 282 | T | G |
| Hole (CA3 #2): any Combination ||||| 
| 352 | 233 | 220 | L | L,K (R,W) |
| 368 | 249 | 236 | T | V |
| Set #4 ||||| 
| Knob (CA3 #1) ||||| 
| 352 | 233 | 220 | L | L (F,Y,M) |
| 368 | 249 | 236 | T | S |
| 370 | 251 | 238 | L | F |
| 414 | 295 | 282 | T | S |
| Hole (CA3 #2): any Combination ||||| 
| 352 | 233 | 220 | L | L,K (R,W) |
| 368 | 249 | 236 | T | S |
| Set #5 ||||| 
| Knob (CA3 #1) ||||| 
| 352 | 233 | 220 | L | W |
| Hole (CA3 #2): any Combination ||||| 
| 352 | 233 | 220 | L | L,K (R) |
| 368 | 249 | 236 | T | G (A) |
| Set #6 ||||| 
| Knob (CA3 #1) ||||| 
| 366 | 247 | 234 | T | S |
| 416 | 397 | 284 | I | F (W) |
| Hole (CA3 #2): any Combination ||||| 
| 352 | 233 | 220 | L | L,K (R,W) |
| 370 | 251 | 238 | L | G (A) |
| 412 | 293 | 280 | A | M (K) |
| 414 | 295 | 282 | T | T (S) |

At each residue position, one or more potential mutations are listed. At each position, a change must be made unless the native amino acid is included in the list of potential mutations; changes in parentheses are alternatives.

Table 2 shows the IgA CA3 domain interface residues for potential charge swaps.

TABLE 2

| Human IgA CA3 Domain Interface Residues Potential Charge Swaps in CA3 Domain | | |
|---|---|---|
| | Chain #1 | Chain #2 |
| FIG. 2 (Bur) | H350D, E | E357K,R |
| IgAl (SEQ ID NO: 1) | H231D, E | E238K, R |
| IgA2 (SEQ ID NO: 2) | H218D, E | E225K, R |
| OR ONE OF | | |
| FIG. 2 (Bur) | H357K,R; R372D, E; R418D, E | |
| IgAl (SEQ ID NO: 1) | H238K,R; R253D, E; R299D, E | |

TABLE 2-continued

| Human IgA CA3 Domain Interface Residues Potential Charge Swaps in CA3 Domain | | |
|---|---|---|
| | Chain #1 | Chain #2 |
| IgA2 (SEQ ID NO: 2) | H225K,R; R240D, E; R286D, E | |
| OR ONE OF | | |
| FIG. 2 (Bur) | | H357K,R; R372D, E; R418D, E |
| IgAl (SEQ ID NO: 1) | | H238K,R; R253D, E; R299D, E |
| IgA2 (SEQ ID NO: 2) | | H225K,R; R240D, E; R286D, E |

Table 3 shows polypeptide sequences referenced in the present application.

TABLE 3

SEQID 1 = sp|P01876|IGHA1-HUMAN Ig alpha-1 chain C region [Homeo sapiens]
ASPTSPKVFPLSLCSTQPDGNVVIACLVQGFFPQEPLSVTWSESGQGVTARNFPPSQDASGDLYTTSSQLTLPATQC
LAGKSVTCHVKHYTNPSQDVTVPCPVPSTPPTPSPSTPPTPSPSCCHPRLSLHRPALEDLLLGSEANLTCTLTGLRD
ASGVTFTWTPSSGKSAVQGPPERDLCGCYSVSSVLPGCAEPWNHGKTFTCTAAYPESKTPLTATLSKSGNTFRPEVH
LLPPPSEELALNELVTLTCLARGFSPKDVLVRWLQGSQELPREKYLTWASRQEPSQGTTTFAVTSILRVAAEDWKKG
DTFSCMVGHEALPLAFTQKTIDRLAGKPTHVNVSVVMAEVDGTCY SEQID 2 = sp|P01877|IGHA2_HUMAN Ig alpha-2 chain C region [Homo sapiens]
ASPTSPKVFPLSLDSTPQDGNVVVACLVQGFFPQEPLSVTWSESGQNVTARNFPPSQDASGDLYTTSSQLTLPATQC
PDGKSVTCHVKHYTNPSQDVTVPCPVPPPPPCCHPRLSLHRPALEDLLLGSEANLTCTLTGLRDASGATFTWTPSSG
KSAVQGPPERDLCGCYSVSSVLPGCAQPWNHGETFTCTAAHPELKTPLTANITKSGNTFRPEVHLLPPPSEELALNE
LVTLTCLARGFSPKDVLVRWLQGSQELPREKYLTWASRQEPSQGTTTFAVTSILRVAAEDWKKGDTFSCMVGHEALP
LAFTQKTIDRMAGKPTHVNVSVVMAEVDGTCY SEQID 3 = gi|21489959|ref|NP_653247.1| immunoglobulin J chain precursor [Homo sapiens]
MKNHLLFWGVLAVFIKAVHVKAQEDERIVLVDNKCKCARITSRIIRSSEDPNEDIVERNIRIIVPLNNRENISDPTS
PLRTRFVYHLSDLCKKCDPTEVELDNQIVTATQSNICDEDSATETCYTYDRNKCYTAVVPLVYGGETKMVETALTPD
ACYPD SEQID 4 = Human IgA2 [Table 1, Set #1, Knob CA3 #1]
ASPTSPKVFPLSLDSTPQDGNVVVACLVQGFFPQEPLSVTWSESGQNVTARNFPPSQDASGDLYTTSSQLTLPATQC
PDGKSVTCHVKHYTNPSQDVTVPCPVPPPPPCCHPRLSLHRPALEDLLLGSEANLTCTLTGLRDASGATFTWTPSSG
KSAVQGPPERDLCGCYSVSSVLPGCAQPWNHGETFTCTAAHPELKTPLTANITKSGNTFRPEVELMPPPSEELALNE
LVTLWCLARGFSPKDVLVRWLQGSQELPREKYLTWASRQEPSQGTTTFAVTSILRVAAEDWKKGDTFSCMVGHEALP
LAFTQKTIDRLAGKPTHVNVSVVMAEVDGTCY SEQID 5 = Human IgA2 [Table 1, Set #1, Hole, CA3 #2]
ASPTSPKVFPLSLDSTPQDGNVVVACLVQGFFPQEPLSVTWSESGQNVTARNFPPSQDASGDLYTTSSQLTLPATQC
PDGKSVTCHVKHYTNPSQDVTVPCPVPPPPPCCHPRLSLHRPALEDLLLGSEANLTCTLTGLRDASGATFTWTPSSG
KSAVQGPPERDLCGCYSVSSVLPGCAQPWNHGETFTCTAAHPELKTPLTANITKSGNTFRPEVHLLPPPSRELALNE
LVTLGCLARGFSPKDVLVRWLQGSQELPREKYLTWASRQEPSQGTTTFAVISILRVAAEDWKKGDTFSCMVGHEALP
LAFTQKTIDRLAGKPTHVNVSVVMAEVDGTCY SEQID 6 = Human CL-kappa
RTVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC SEQID 7 - Human CL-lambda
GQPKAAPSVTLFPPSSEELQANKATLVCLISDFYPGAVTVAWKADSSPVKAGVETTTPSKQSNNKYAASSYLSLTPE
QWKSHRSYSCQVTHEGSTVEKTVAPTECS SEQID 8 = Human IgA2 [Table 1, Set #1, Hole, CA3 #2] for use with VL domain
SSASPTSPKVFPLSLDSTPQDGNVVVACLVQGFFPQEPLSVTWSESGQNVTARNFPPSQDASGDLYTTSSQLTLPAT
QCPDGKSVTCHVKHYTNPSQDVTVPCPVPPPPPCCHPRLSLHRPALEDLLLGSEANLTCTLTGLRDASGATFTWTPS
SGKSAVQGPPERDLCGCYSVSSVLPGCAQPWNHGETFTCTAAHPELKTPLTANITKSGNTFRPEVHLLPPPSRELAL
NELVTLGCLARGFSPKDVLVRWLQGSQELPREKYLTWASRQEPSQGTTTFAVISILRVAAEDWKKGDTFSCMVGHEA
LPLAFTQKTIDRLAGKPTHVNVSVVMAEVDGTCY SEQID 9 = Human CL-kappa for use with VH domain
ASVAAPSVFIFPPSDEQLKSGTASVVCLLNNFYPREAKVQWKVDNALQSGNSQESVTEQDSKDSTYSLSSTLTLSKA
DYEKHKVYACEVTHQGLSSPVTKSFNRGEC
IgA2 for Example 4 (SEQIDs 9-12)
RSV F x G
anti-F MEDI-493 (Palivizumab, Synagis)
anti-G 3G12 US7736648 Seq 29 & 43

SEQID 10 = U57736648 3G12 VH - human IgA2 [Table 1, Set #1, Knob, CA3 #1]
QLQLQESGPGLVKPSETLSLTCTVSGGSISSSNYYWGWIRQPPGKGLEWIASIHDSGSIYYNPSLRSRVTISVDTSK TABLE 3-continued

```
NQFSLKLSSVTAADTAVYYCARHLVWFGELRNNWFDPWGQGTLVTVASASPTSPKVFPLSLDSTPQDGNVVVACLVQ
GFFPQEPLSVTWSESGQNVTARNFPPSQDASGDLYTTSSQLTLPATQCPDGKSVTCHVKHYTNPSQDVTVPCPVPPP
PPCCHPRLSLHRPALEDLLLGSEANLTCTLTGLRDASGATFTWTPSSGKSAVQGPPERDLCGCYSVSSVLPGCAQPW
NHGETFTCTAAHPELKTPLTANITKSGNTFRPEVELMPPPSEELALNELVTLWCLARGFSPKDVLVRWLQGSQELPR
EKYLTWASRQEPSQGTTTFAVTSILRVAAEDWKKGDTFSCMVGHEALPLAFTQKTIDRLAGKPTHVNVSVVMAEVDG
TOY

SEQID 11 = U57736648 3G12 VL - human CL-kappa
EIVMTQSPATLSVSPGERATLSCRASQSVNSNLAWYQHKPGQAPRLLIYGASTRATGIPARFSGSGSGTDFTLTISS
LQSEDFAVYYCQQYNNWPLFGPGTKVDLKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC SEQID 12 = palivizumab VL - human IgA2 [Table 1, Set #1, Hole, CA3 #2, CA1
CrossmAb]
DIQMTQSPSTLSASVGDRVTITCKCQLSVGYMHWYQQKPGKAPKLLIYDTSKLASGVPSRFSGSGSGTEFTLTISSL
QPDDFATYYCFQGSGYPFTFGGGTKLEIKSSASPTSPKVFPLSLDSTPQDGNVVVACLVQGFFPQEPLSVTWSESGQ
NVTARNFPPSQDASGDLYTTSSQLTLPATQCPDGKSVTCHVKHYTNPSQDVTVPCPVPPPPPCCHPRLSLHRPALED
LLLGSEANLTCTLTGLRDASGATFTWTPSSGKSAVQGPPERDLCGCYSVSSVLPGCAQPWNHGETFTCTAAHPELKT
PLTANITKSGNTFRPEVHLLPPPSRELALNELVTLGCLARGFSPKDVLVRWLQGSQELPREKYLTWASRQEPSQGTT
TFAVISILRVAAEDWKKGDTFSCMVGHEALPLAFTQKTIDRLAGKPTHVNVSVVMAEVDGTCY SEQID 13 = palivizumab VH - human CL-kappa CrossmAb
QVTLRESGPALVKPTQTLTLTCTFSGFSLSTSGMSVGWIRQPPGKALEWLADIWWDDKKDYNPSLKSRLTISKDTSK
NQVVLKVTNMDPADTATYYCARSMITNWYFDVWGAGTTVTVSSASVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSFNRGEC
IgA2 for Example 5 (SEQIDs 13-16)
Influenza HA X HA
U520140120113 Crucell anti-influenza virus seq 62 & 64
U520140248286 Genentech anti-hemagglutinin seq 234 & 235

SEQID 14 = U520140120113 Seq 62 VH - human IgA2 [Table 1, Set #1, Knob, CA3
#1]
QVQLVQSGAEVKKPGSSVKVSCKSSGGTSNNYAISWVRQAPGQGLDWMGGISPIFGSTAYAQKFQGRVTISADIFSN
TAYMELNSLTSEDTAVYFCARHGNYYYSGMDVWGQGTTVTVSSASPTSPKVFPLSLDSTPQDGNVVVACLVQGFFP
QEPLSVTWSESGQNVTARNFPPSQDASGDLYTTSSQLTLPATQCPDGKSVTCHVKHYTNPSQDVTVPCPVPPPPPCC
HPRLSLHRPALEDLLLGSEANLTCTLTGLRDASGATFTWTPSSGKSAVQGPPERDLCGCYSVSSVLPGCAQPWNHGE
TFTCTAAHPELKTPLTANITKSGNTFRPEVELMPPPSEELALNELVTLWCLARGFSPKDVLVRWLQGSQELPREKYL
TWASRQEPSQGTTTFAVTSILRVAAEDWKKGDTFSCMVGHEALPLAFTQKTIDRLAGKPTHVNVSVVMAEVDGTCY SEQID 15 = U520140120113 Seq 64 VL - human CL-lambda
SYVLTQPPAVSGTPGQRVTISCSGSDSNIGRRSVNWYQQFPGTAPKLLIYSNDQRPSVVPDRFSGSKSGTSASLAIS
GLQSEDEAEYYCAAWDDSLKGAVFGGGTQLTVLGQPKAAPSVTLFPPSSEELQANKATLVCLISDFYPGAVTVAWKA
DSSPVKAGVETTTPSKQSNNKYAASSYLSLTPEQWKSHRSYSCQVTHEGSTVEKTVAPTECS SEQID 16 = U520140248286 Seq 235 VL - human IgA2 [Table 1, Set #1, Hole, CA3
1, CA1 CrossmAb]
EIVLTQSPATLSVSPGERATLSCRASQVISHNLAWYQQKPGQAPRLLIYGASTRASGIPARFSGSGSGTDYTLTITS
LQSEDFAVYYCQHYSNWPPRLTFGGGTKVEIKSSASPTSPKVFPLSLDSTPQDGNVVVACLVQGFFPQEPLSVTWSE
SGQNVTARNFPPSQDASGDLYTTSSQLTLPATQCPDGKSVTCHVKHYTNPSQDVTVPCPVPPPPPCCHPRLSLHRPA
LEDLLLGSEANLTCTLTGLRDASGATFTWTPSSGKSAVQGPPERDLCGCYSVSSVLPGCAQPWNHGETFTCTAAHPE
LKTPLTANITKSGNTFRPEVHLLPPPSRELALNELVTLGCLARGFSPKDVLVRWLQGSQELPREKYLTWASRQEPSQ
GTTTFAVISILRVAAEDWKKGDTFSCMVGHEALPLAFTQKTIDRLAGKPTHVNVSVVMAEVDGTCY SEQID 17 = US20140248286 Seq 234 VH - human CL-kappa CrossmAb
EVQLVESGGGVVQPGKSLRLSCAASGLTFSSYAVHWVRQAPGKGLEWVTLISYDGANQYYADSVKGRFTISRDNSKN
TVYLQMNSLRPEDTAVYYCAVPGPVFGIFPPWSYFDNWGQGILVTVSSASVAAPSVFIFPPSDEQLKSGTASVVCLL
NNFYPREAKVQWKVDNALQSGNSQESVTEQDSKDSTYSLSSTLTLSKADYEKHKVYACEVTHQGLSSPVTKSFNRGE
C
IgA2 for Example 6 (SEQIDs 17-20)
Anti-C. difficile
anti-TxA 3D8 U57625559 Seq 1 & 4
anti-TxB 124-152 U57625559 Seq 54 & 58

SEQID 18 = U57625559 anti-Cdiff-TxA 3D8 Seq 1 VH - human IgA2 [Table 1, Set
#1, Knob, CA3 #1]
QVQLVESGGGVVQPGRSLRLSCAASGFSFSNYGMHWVRQAPGKGLEWVALIWYDGSNEDYTDSVKGRFTISRDNSKN
TLYLQMNSLRAEDTAVYYCARWGMVRGVIDVFDIWGQGTVVTVSSASPTSPKVFPLSLDSTPQDGNVVVACLVQGFF
PQEPLSVTWSESGQNVTARNFPPSQDASGDLYTTSSQLTLPATQCPDGKSVTCHVKHYTNPSQDVTVPCPVPPPPPC
CHPRLSLHRPALEDLLLGSEANLTCTLTGLRDASGATFTWTPSSGKSAVQGPPERDLCGCYSVSSVLPGCAQPWNHG
ETFTCTAAHPELKTPLTANITKSGNTFRPEVELMPPPSEELALNELVTLWCLARGFSPKDVLVRWLQGSQELPREKY
LTWASRQEPSQGTTTFAVTSILRVAAEDWKKGDTFSCMVGHEALPLAFTQKTIDRLAGKPTHVNVSVVMAEVDGTCY SEQID 19 = U57625559 anti-Cdiff-TxA 3D8 Seq 4 VL - human CL-kappa
DIQMTQSPSSVSASVGDRVTITCRASQGISSWLAWYQHKPGKAPKLLIYAASSLQSGVPSRFSGSGSGTDFTLTISS
LQPEDFATYYCQQANSPPWTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC SEQID 20 = U57625559 anti-Cdiff-TxB 124-152 Seq 58 VL - human IgA2 [Table 1,
Set #1, Hole, CA3 #2, CA1 CrossmAb]
EIVLTQSPGTLSLSPGERATLSCRASQSVSSSYLAWYQQKPGQAPRLLIYGASSRATGIPDRFSGSGSGTDFTLTIS
```

TABLE 3-continued

```
RLEPEDFAVYYCQQYGSSTWTFGQGTKVEIKSSASPTSPKVFPLSLDSTPQDGNVVVACLVQGFFPQEPLSVTWSES
GQNVTARNFPPSQDASGDLYTTSSQLTLPATQCPDGKSVTCHVKHYTNPSQDVTVPCPVPPPPPCCHPRLSLHRPAL
EDLLLGSEANLTCTLTGLRDASGATFTWTPSSGKSAVQGPPERDLCGCYSVSSVLPGCAQPWNHGETFTCTAAHPEL
KTPLTANITKSGNTFRPEVHLLPPPSRELALNELVTLGCLARGFSPKDVLVRWLQGSQELPREKYLTWASRQEPSQG
TTTFAVISILRVAAEDWKKGDTFSCMVGHEALPLAFTQKTIDRLAGKPTHVNVSVVMAEVDGTCY

SEQID 21 = U57625559 anti-Cdiff-TxB 124-152 Seq 54 VH - human CL-kappa
CrossmAb
EVQLVQSGAEVKKSGESLKISCKGSGYSFTSYWIGWVRQMPGKGLEWMGIFYPGDSSTRYSPSFQGQVTISADKSVN
TAYLQWSSLKASDTAMYYCARRRNWGNAFDIWGQGTMVTVSSASVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGEC SEQID 22 = Human IgG1
STKGPSVFPLAPSSKSTSGGTAALGCLVKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLYSKLTVDKSRWQQGNVFSCS
VMHEALHNHYTQKSLSLSPGK SEQID 23 = Example 1
QVQLQQSGAELARPGASVKMSCKASGYTFTRYTMHWVKQRPGQGLEWIGYINPSRGYTNYNQKFKDKATLTTDKSSS
TAYMQLSSLTSEDSAVYYCARYYDDHYCLDYWGQGTTLTVSSASPTSPKVFPLSLCSTQPDGNVVIACLVQGFFPQE
PLSVTWSESGQGVTARNFPPSQDASGDLYTTSSQLTLPATQCLAGKSVTCHVKHYTNPSQDVTVPCPVPSTPPTPSP
STPPTPSPSCCHPRLSLHRPALEDLLLGSEANLTCTLTGLRDASGVTFTWTPSSGKSAVQGPPERDLCGCYSVSSVL
PGCAEPWNHGKTFTCTAAYPESKTPLTATLSKSGNTFRPEVHLLPPPSEELALNELVTLTCLARGFSPKDVLVRWLQ
GSQELPREKYLTWASRQEPSQGTTTFAVTSILRVAAEDWKKGDTFSCMVGHEALPLAFTQKTIDRLAGKPTHVNVSV
VMAEVDGTCY SEQID 24 = Example 1
GEQKLISEEDLGGGGSTPPTPSPSTPPTPSPSCCHPRLSLHRPALEDLLLGSEANLTCTLTGLRDASGVTFTWTPSS
GKSAVQGPPERDLCGCYSVSSVLPGCAEPWNHGKTFTCTAAYPESKTPLTATLSKSGNTFRPEVHLLPPPSEELALN
ELVTLTCLARGFSPKDVLVRWLQGSQELPREKYLTWASRQEPSQGTTTFAVTSILRVAAEDWKKGDTFSCMVGHEAL
PLAFTQKTIDRLAGKPTHVNVSVVMAEVDGTCY SEQID 25 = Example 1
QVQLQQPGAELVKPGASVKMSCKASGYTFTSYNMHWVKQTPGRGLEWIGAIYPGNGDTSYNQKFKGKATLTADKSSS
TAYMQLSSLTSEDSAVYYCARSTYYGGDWYFNVWGAGTTVTVSASVAAPSVFIFPPSDEQLKSGTASVVCLLNNFYP
REAKVQWKVDNALQSGNSQESVTEQDSKDSTYSLSSTLTLSKADYEKHKVYACEVTHQGLSSPVTKSFNRGECPVPS
TPPTPSPSTPPTPSPSCCHPRLSLHRPALEDLLLGSEANLTCTLTGLRDASGVTFTWTPSSGKSAVQGPPERDLCGC
YSVSSVLPGCAEPWNHGKTFTCTAAYPESKTPLTATLSKSGNTFRPEVHLLPPPSEELALNELVTLTCLARGFSPKD
VLVRWLQGSQELPREKYLTWASRQEPSQGTTTFAVTSILRVAAEDWKKGDTFSCMVGHEALPLAFTQKTIDRLAGKP
THVNVSVVMAEVDGTCY SEQID 26 = Example 1
QIVLTQSPAIMSASPGEKVTMTCSASSSVSYMNWYQQKSGTSPKRWIYDTSKLASGVPAHFRGSGSGTSYSLTISGM
EAEDAATYYCQQWSSNPFTFGSGTKLEINRAVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC SEQID 27 = Example 1
QIVLSQSPAILSASPGEKVTMTCRASSSVSYIHWFQQKPGSSPKPWIYATSNLASGVPVRFSGSGSGTSYSLTISRV
EAEDAATYYCQQWTSNPPTFGGGTKLEIKSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKSC
```

DETAILED DESCRIPTION OF THE INVENTION

I. Definitions

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

All publications mentioned herein are expressly incorporated herein by reference to disclose and describe the methods and/or materials in connection with which the publications are cited.

The term "antigen" refers to an entity or fragment thereof, which can bind to an antibody or trigger a cellular immune response. An immunogen refers to an antigen, which can elicit an immune response in an organism, particularly an animal, more particularly a mammal including a human. The term antigen includes regions known as antigenic determinants or epitopes.

As used herein, the term "immunogenic" refers to substances, which elicit the production of antibodies, and/or activate T-cells and/or other reactive immune cells directed against an antigen of the immunogen.

An immune response occurs when an individual produces sufficient antibodies, T-cells and other reactive immune cells in response to administered immunogenic compositions of the present invention to moderate or alleviate the disorder to be treated.

The term immunogenicity as used herein refers to a measure of the ability of an antigen to elicit an immune response (humoral or cellular) when administered to a recipient. The present invention is concerned with approaches that reduce the immunogenicity of the subject human chimeric or humanized antibodies.

The term "antibody" includes monoclonal antibodies (including full length antibodies which have an immunoglobulin Fc region), single-chain molecules, as well as antibody fragments (e.g., Fab, F(ab')$_2$, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains.

In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for µ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site.

Serum IgA is a monomer but can also polymerize. In its secretory form IgA comprises from 2-5 of the basic 4-chain units, linked by a J chain, which may include a tail-piece, and may be associated by a secretory component. The structures of tail-piece, dimeric IgA and secretory IgA, associated with a secretory component (sIgA) are illustrated in FIG. 1. IgA antibodies can be further divided into IgA1 and IgA2 sub-classes, which are expressly included in the definition of "IgA".

The L chain from any vertebrate species can be assigned to one of two clearly distinct types, called kappa (κ) and lambda (λ), based on the amino acid sequences of their constant domains.

FIGS. 2A-2C show the alignment of human IgG1 IgA1 and IgA2 Fc CG1/CA1, CG2/CA2, and CG3/CA3 constant domains, respectively. In the Figures, the human IgG1 sequence is from J00228 (Takahashi N., et al. Cell 29:671-679 (1982)), and the IgG sequence is numbered according to PDB 1OQO beta strand (s) and alpha-helix (h) assignments from PDB 1OQO. The human IgA sequence and numbering is from PDB 2QEJ (Ramsland P. A., et al., Proc Natl Acad Sci USA 104:15051-15056 (2007) and from IgA BUR (Putnam W. F., et al. J. Biol. Chem. 254:2865-2874 (1979)). The human IgG1 constant region sequence is assigned SEQ ID NO: 19; the IgA1 constant region sequence is shown as SEQ ID NO: 1 and the human IgA2 constant region sequence is shown as SEQ ID NO: 2. Throughout the disclosure, the amino acid positions are numbered according to these alignments.

For further details of the structure and properties of the different classes of antibodies, see e.g., Basic and Clinical Immunology, 8th Edition, Daniel P. Stites, Abba I. Terr and Tristram G. Parslow (eds), Appleton & Lange, Norwalk, Conn., 1994, page 71 and Chapter 6.

Unless stated otherwise, the term "antibody" specifically includes native human and non-human IgG1, IgG2, IgG3, IgG4, IgE, IgA1, IgA2, IgD and IgM antibodies, including naturally occurring variants.

The term "IgA" antibody is used herein to specifically include all sub-classes, i.e. IgA1 and IgA2 antibodies, including dimeric and multimeric forms, with and without a secretory component. Of the two sub-classes IgA2 is more stable than IgA1 since its shorter hinge region renders it resistant to certain bacterial proteases. This shorter hinge also explains a rigid and non-planar structure which facilitates better multivalent binding of IgA2 to antigens on bacterial surfaces. For the purposes of the present invention, the IgA antibody may be IgA 1 or IgA2, and preferably is a dimer, where two tail-pieces preferably are connected by a J chain (see, FIG. 1, SEQ ID NO: 3). In the IgA binding molecules of the present invention, the J chain may be a full-length native J chain, but may also contain amino acid alterations, such as substitutions, insertions, deletions, truncations, specifically including J chain fragments, as long as the J chain remains functional. Inclusion of a full-length native J-chain is preferred for the purposes of the present invention.

The term "functional" in connection with a modified J chain means that the J chain retains the primary function of a native J chain, e.g. a native human J chain, in particular, the ability to enable efficient polymerization (dimerization) of IgA and binding of such polymers (dimers) to the secretory component (SC)/polymeric (p)IgR.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in Clackson et at (1991) *Nature* 352:624-628 and Marks et al. (1991) *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA* 81:6851-6855).

"Humanized" forms of non-human (e.g., murine) antibodies are antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are also replaced by corresponding non-human residues.

Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

As used herein, "antibody mutant" or "antibody variant" refers to an amino acid sequence variant of a reference antibody wherein one or more of the amino acid residues of the reference antibody have been modified. The reference antibody can, for example, be a native antibody but also a known variant of a native antibody. Such mutants necessarily have less than 100% sequence identity or similarity with the reference antibody. In a preferred embodiment, the antibody mutant will have an amino acid sequence having at least 75% amino acid sequence identity or similarity with the amino acid sequence of either the heavy or light chain variable domain of the reference antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties) with the reference antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" antibody herein is one which has been identified and separated and/or recovered from a component of its natural environment in a recombinant host cell. Contaminant components of its natural environment are materials which would interfere with diagnostic or therapeutic uses for the antibody, and may include enzymes, hormones, and other proteinaceous or nonproteinaceous solutes, as well as undesired byproducts of the production. Thus, in the case of bi- or multi-specific IgA antibodies undesired byproducts include monospecific binding units (AA and/or BB in the case of a bispecific antibody comprising AB binding units), and multimers not comprising the desired number of subunits. In preferred embodiments, a bi- or multi-specific antibody will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of a amino acid sequencer, or (3) to homogeneity by SDS-PAGE under reducing or non-reducing conditions using Coomassie blue or, preferably, silver stain. Ordinarily, an isolated bispecific binding molecule, e.g. antibody, will be prepared by at least one purification step.

The term "specific binding" or "specifically binds to" or is "specific for" refers to the binding of an antibody to a target molecule (antigen), e.g., an epitope on a particular polypeptide, peptide, or other target (e.g. a glycoprotein target), and means binding that is measurably different from a non-specific interaction (e.g., a non-specific interaction may be binding to bovine serum albumin or casein). Specific binding can be measured, for example, by determining binding of antibody to a target molecule compared to binding of antibody to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "Kd" or "Kd value" refers to a dissociation constant measured by a technique appropriate for the antibody and target pair, for example using surface plasmon resonance assays, for example, using a BIAcore™-2000 or a BIAcore™-3000 (BIAcore, Inc., Piscataway, N.J.) at 25° C. with immobilized antigen CM5 chips at about 10 response units (RU).

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, covalent linkage being preferred.

The term "multi-specific IgA" is used herein in the broadest sense to refer to IgA antibodies with two or more binding specificities. Thus, the term "multi-specific" includes "bispecific", e.g. bispecific antibodies or bispecific binding units, including IgA dimers comprising two monospecific subunits, each binding to a different antigen (AA, BB), or two bispecific subunits, each binding to two different antigens (AB, AB).

The term "binding unit" is used herein to refer to a molecule comprising a pair of IgA heavy chain constant region polypeptides each comprising at least a CA3 domain, and each conjugated to a binding region (antibody variable region) to a binding target, e.g. a target antigen. In one embodiment, the dimeric IgA molecules of the present invention consist of two monospecific binding units, each binding unit having binding specificity to a different binding target (AA, BB). In another embodiment, in the dimeric IgA molecules of the present invention at least one of the two binding units has two different binding specificities (i.e. is a bispecific, e.g. AA, A,B or AA, BC). In another embodiment, each of the two binding units has two specificities, which may be the same (AB, AB) or different (AC, CD or AB, AC, for example).

The term "bispecific IgA antibody binding unit" is used in the broadest sense and specifically covers a pair of IgA antibody heavy chain constant region polypeptides, comprising at least a CA3 constant domain, fused to a variable domain sequence ($V_H$), each variable domain sequence binding to a different target, with or without associated antibody light chain variable domain ($V_L$) sequences. In one embodiment, the bispecific IgA antibody comprises two $V_H V_L$ antigen binding regions, each capable of binding to a different epitope on one antigen or epitopes on two different antigens. The bispecific IgA antibody binding units can be full length from a single species, or be chimerized or humanized.

A "full length IgA antibody heavy chain" is a polypeptide consisting in N-terminal to C-terminal direction of an antibody heavy chain variable domain (VH), an antibody constant heavy chain constant domain 1 (CA1 or Cα1), an antibody constant heavy chain constant domain 2 (CA2 or Cα2), and an antibody heavy chain constant domain 3 (CA3 or Cα3). The bi- or multi-specific full length IgA antibodies according to the invention comprise two monomers (binding units), each of which may be mono- or bispecific, with or without a secretory component. Thus, the multi-specific IgA antibodies of the present invention may include monospecific and bispecific binding units, provided that the resultant IgA antibody has at least two binding specificities. The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

The term "valent" as used herein denotes the presence of a specified number of binding sites in an antibody. As such, the terms "bivalent", "tetravalent", and "hexavalent" denote the presence of two binding sites, four binding sites, and six binding sites, respectively. Thus, if in a bispecific IgA antibody according to the present invention each binding unit is bivalent, the bispecific IgA antibody will have 4 valencies.

The term "epitope" includes any molecular determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. A "binding region" is a region on a binding target bound by a binding molecule.

"Polyepitopic specificity" refers to the ability to specifically bind to two or more different epitopes on the same or different target(s). "Monospecific" refers to the ability to bind only one epitope. According to one embodiment the bispecific IgM antibody binds to each epitope with an affinity of at least $10^{-7}$M, or $10^{-8}$ M or better.

The term "target" or "binding target" is used in the broadest sense and specifically includes polypeptides, nucleic acids, carbohydrates, lipids, and other molecules with biological function as they exist in nature. The "target" may, for example, be a cell, wherein the bispecific binding units target two different cell types, different subpopulations of the same cell type (e.g. different B-cell populations) or two different entities on a single cell.

An "antigen-binding site" or "antigen-binding region" of an antibody of the present invention typically contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer CDRs (i.e., where binding specificity is determined by three, four or five CDRs). Less than a complete set of 6 CDRs may be sufficient for binding to some binding targets. Thus, in some instances, the CDRs of a VH or a VL domain alone will be sufficient. Furthermore, certain antibodies might have non-CDR-associated binding sites for an antigen. Such binding sites are specifically included within the present definition.

The term "interface", as used herein, is used to refer to a region, which comprises those "contact" amino acid residues (or other non-amino acid groups such as, for example, carbohydrate groups,) in a first IgA heavy chain constant region which interact with one or more "contact" amino acid residues (or other non-amino acid groups) in a second IgA heavy chain constant region.

The term "asymmetric interface" is used to refer to an interface (as hereinabove defined) formed between two antibody chains, such as a first and a second IgA heavy chain constant region and/or between an IgA heavy chain constant region and its matching light chain, wherein the contact residues in the first and the second chains are different by design, comprising complementary contact residues. The asymmetric interface can be created by knobs/holes interactions and/or salt bridges coupling (charge swaps) and/or other techniques known in the art, such as for example, by the CrossMab approach for coupling an a heavy chain to its matching light chain.

A "cavity" or "hole" refers to at least one amino acid side chain which is recessed from the interface of the second polypeptide and therefore accommodates a corresponding protuberance ("knob") on the adjacent interface of the first polypeptide. The cavity (hole) may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The preferred import residues for the formation of a cavity are usually naturally occurring amino acid residues and are preferably selected from alanine (A), serine (S), threonine (T), valine (V) and glycine (G). Most preferred amino acid residues are serine, alanine or threonine, most preferably alanine. In the preferred embodiment, the original residue for the formation of the protuberance has a large side chain volume, such as tyrosine (Y), arginine (R), phenylalanine (F) or tryptophan (W).

An "original" amino acid residue is one which is replaced by an "import" residue which can have a smaller or larger side chain volume than the original residue. The import amino acid residue can be a naturally occurring or non-naturally occurring amino acid residue, but preferably is the former.

By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991), for example. To generate such non-naturally occurring amino acid residues, the procedures of Noren et al. Science 244: 182 (1989) and Ellman et al., supra can be used. Briefly, this involves chemically activating a suppressor tRNA with a non-naturally occurring amino acid residue followed by in vitro transcription and translation of the RNA. The methods of the current invention, in certain embodiments, involve replacing at least one original amino acid residue in an IgM heavy chain, but more than one original residue can be replaced. Normally, no more than the total residues in the interface of the first or second polypeptide will comprise original amino acid residues which are replaced. The preferred original residues for replacement are "buried". By "buried" is meant that the residue is essentially inaccessible to solvent. The preferred import residue is not cysteine to prevent possible oxidation or mispairing of disulfide bonds.

The protuberance is "positionable" in the cavity which means that the spatial location of the protuberance and cavity on the interface of the first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art, including techniques of molecular modeling.

By "original nucleic acid" is meant the nucleic acid encoding a polypeptide of interest which can be "altered" (i.e. genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest.

Normally, a codon encoding an original residue is replaced by a codon encoding an import residue. Techniques for genetically modifying a DNA in this manner have been reviewed in Mutagenesis: a Practical Approach, M. J. McPherson, Ed., (IRL Press, Oxford, UK. (1991), and include site-directed mutagenesis, cassette mutagenesis and polymerase chain reaction (PCR) mutagenesis, for example.

The protuberance or cavity can be "introduced" into the interface of the first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. According, the protuberance or cavity which is "introduced" is "non-naturally occurring" or "non-native", which means that it does not exist in nature or in the original polypeptide (e.g. a humanized monoclonal antibody).

Preferably the import amino acid residue for forming the protuberance has a relatively small number of "rotamers" (e.g. about 3-6). A "rotamer" is an energetically favorable conformation of an amino acid side chain. The number of rotamers for the various amino acid residues are reviewed in Ponders and Richards, J. Mol. Biol. 193: 775-791 (1987).

The term "host cell" as used in the current application denotes any kind of cellular system which can be engineered to generate the antibodies according to the current invention. In one embodiment Chinese hamster ovary (CHO) cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "effective amount" is used herein refers to an amount of a drug or drug combination effective to treat a target disease in a subject, such as a human patient. The effective amount of the drug may cure and/or reduce the severity and/or duration of the target disease, and may invoke a partial response (PR) or complete response (CR).

DETAILED DESCRIPTION

Immunoglobulin A (IgA), as the major class of antibody present in the mucosal secretions of most mammals, represents a key first line of defense against invasion by inhaled and ingested pathogens. IgA is also found at significant concentrations in the serum of many species, where it functions as a second line of defense mediating elimination of pathogens that have breached the mucosal surface. Receptors specific for the Fc region of IgA, FcαR, are key mediators of IgA effector function.

Human IgA may have two different IgA heavy constant region (Ca) genes which give rise to the two subclasses, IgA 1 and IgA2. The main difference between IgA1 and IgA2 resides in the hinge region that lies between the two Fab arms and the Fc region. IgA 1 has an extended hinge region due to the insertion of a duplicated stretch of amino acids, which is absent in IgA2. The sequence of human IgA1 heavy chain constant region is shown as SEQ ID NO: 1. The sequence of human IgA2 heavy chain constant region is shown as SEQ ID NO: 2.

IgA has the capacity to form dimers, in which two monomer units, each comprising two heavy chains and light chains, are arranged in an end-to-end configuration stabilized by disulphide bridges and incorporation of a J (joining) chain. The sequence of native human J chain is shown as SEQ ID NO: 3. Dimeric IgA, produced locally at mucosal sites, is transported across the epithelial cell boundary and out into the secretions by interaction with the polymeric immunoglobulin receptor (pIgR). During this process the pIgR is cleaved and the major fragment, termed secretory component (SC), becomes covalently attached to the IgA dimer.

The multi-specific IgA molecules of the present invention are based on the dimeric form of an IgA antibody, in which two pairs of IgA heavy chain sequences may be present with or without associated light chain sequences. In a preferred embodiment, the IgA binding molecules herein are bispecific, composed of two IgA (IgA1 or IgA2) dimers, including a J chain.

The multi-specific IgA antibodies of the present invention may include mono- and bispecific binding units as long as the molecule as a whole has at least two binding specificities.

Thus, in one embodiment, the IgA antibody herein is bispecific and consists of two monospecific binding units (AA, BB), each having binding specificity to a different binding target.

In another embodiment, the IgA antibody herein comprises two bispecific binding units, each binding unit binding to the same two binding targets (AB, AB) to form a bispecific IgA antibody.

In a further embodiment, one binding unit present in an IgA antibody of the present invention is monospecific (AA) while the other binding units are bispecific (BC), resulting in an IgA antibody with three (A, B, C) binding specificities.

In a different embodiment, each binding unit is bispecific, but one specificity is overlapping (e.g. AB, AC), resulting in an IgA antibody with three (A, B, C) binding specificities.

In a still further embodiment, each binding unit is bispecific with different binding specificities (AB, CD). Thus, the IgA molecule has four (A, B, C, D) binding specificities.

The binding units of the IgA binding molecules herein comprise at least a CA3 (Cα3) domain and may additionally comprise a CA2 (Cα2) domain.

In one embodiment, the multi-specific IgA antibodies of the present invention contain a complete IgA heavy (a) chain constant domain, with one or more modifications to create an asymmetric interface between two heavy chains.

In a further embodiment, the multi-specific IgA antibodies of the present invention comprise a complete native J chain. The J chain is a key protein in the generation of SIgA because it promotes polymerization of IgA and because its presence in these polymers is believed to be required for their affinity to SC/pIgR. The multi-specific IgA antibodies herein may comprise a J chain fragment, or an otherwise modified J chain, as long as the fragment or modified J chain retains the function of native J chain, in particular to enable efficient polymerization of IgA and binding of such polymers to the secretory component (SC)/polymeric (p)IgR. For further details of the structure-function relationship of J chain see. e.g. Johansen et al., 2001; J. Immunol. 167(9): 5185-5192.

In order to generate an IgA molecule with two different a heavy chains (i.e. where at least one of the binding units is bispecific), a solution must be found for coupling the two matching a heavy chains with two different binding specificities to each other. In addition, if a light chain is needed to form a binding region, a solution must be found to couple each heavy chain with its matching light chain to provide the desired binding specificity.

The coupling can be achieved by salt bridge pairs charge switching (also referred to as charge swaps or charge reversals) between certain residues and/or by creating knobs-holes interactions between the two chains. The heavy chains can also be paired with their matching light chains by using the CrossMab technique. The different approaches can also be combined in order to achieve an optimal result.

1. Knobs-into-Holes Technique

To improve the yields of the penta- or hexameric bispecific binding molecules of the present invention, the IgA heavy chain constant regions, e.g. the Cα3 domains, can be altered by the "knob-into-holes" technique which is described in detail with several examples in e.g. WO 96/027011, Ridgway, J., B., et al., Protein Eng 9 (1996) 617-621; and Merchant, A. M., et al., Nat Biotechnol 16 (1998) 677-681. In this method the interaction surfaces of two IgA heavy chain constant domains are altered to increase the heterodimerization of two heavy chains with different binding specificities and/or between a heavy chain and its matching light chain. Each of the two heavy chain domains, can be the "knob", while the other is the "hole". The introduction of a disulfide bridge stabilizes the heterodimers (Merchant, A. M., et al., Nature Biotech 16 (1998) 677-681; Atwell, S., et al., J. Mol. Biol. 270 (1997) 26-35) and increases the yield. Similarly, the matching heavy and light chains can be coupled to each other by this technique (Zhu, Z.; Presta, L. G.; Zapata, G.; Carter, P. *Remodeling domain interfaces to enhance heterodimer formation.* Prot. Sci. 6:781-788 (1997)).

Following this approach, within the original interface of the Cα (e.g. Cα3) domains of one heavy chain that meets the original interface of the corresponding domain of the other heavy chain within the bispecific IgA antibody, an amino acid residue may be replaced with an amino acid residue having a larger side chain volume, thereby creating a protuberance within the interface, which is positionable in a cavity within the interface of the corresponding domain in the other IgA heavy chain constant region. Similarly, the second IgA heavy chain may be altered, by replacing an amino acid residue within the interface with a corresponding domain in the constant region of the first IgA heavy chain, with an amino acid residue having a smaller side chain volume, thereby creating a hole (cavity) within the interface between the two heavy chain regions.

Human IgA Cα3 domain interface residues in knobs-holes positions are shown in Table 1. The Table identifies the native residue at the indicated positions of the Cα3 sequence shown in FIG. 4, following the numbering shown in FIG. 4, as well as the potential mutations that can be used to create knobs-holes pairs. Thus, for example, in the Cα3 domain the native leucine (L) residue in position 352 may be mutated into methionine (M) or the native threonine (T) residue at position 368 may be mutated into tryptophan (W) to create a knob, where the knob mutation can be combined with any combinations of holes listed for amino acid positions 352, 368, and 414.

It is emphasized that the listed knobs-holes mutations in Sets #1-6 can be used in various combinations as set forth in Table 1. Furthermore, the listed mutations can be combined with other knobs-holes and/or charge swap and/or charge introduction mutations, such as the charge swap mutations listed in Table 2. Thus, one or more of the knobs-holes mutations set forth in Table 1 can be combined with one or more of the charge swap mutations listed in Table 2, as discussed herein below. Thus, one can select any set from Table 1 and mix it with any set from Table 2, in any order or combination.

2. Salt Bridge Pairs Charge Switching (Charge Swapping)

Opposite charges attract and similar charges repel each other. The charge of an amino acid molecule is pH dependent and can be characterized by the pK values, which are determined for the alpha amino group (N), the alpha carboxy group (C) and the side chain for free amino acids. The local environment can alter the $pK_a$ of a side chain when the amino acid is part of a protein or peptide.

The charge properties of an amino acid molecule can also be characterized by the isoelectric point (pI), which is the pH at which the overall charge of the molecule is neutral. Since amino acids differ from each other in their side chains, the pI reflects differences in the pKs of the side chains.

Most amino acids (15 out of 20) have a pI close to 6 so they are regarded as having neutral overall charge. Asp and Glu are negatively charged, and His, Lys, Arg are positively charged.

Positions and amino acid residues for charge swapping or charge introduction mutations are listed in Table 2. As discussed above, or more of these mutations, or sets of mutations, can be combined with one or more sets of knobs-holes mutations to provide a desired asymmetric interface between two different IgA heavy chains and/or between an IgA heavy chain and its matching light chain.

Preferably, the asymmetric interface between two different IgA heavy chain constant regions is created by up to 8, such as, for example, 1-8, or 1-7, or 1-6, or 1-5, or 1-4, or 1-3, or 1-2 mutations in one IgA heavy chain, or 2-10, or 2-9, or 2-8, or 2-7, or 2-6, or 2-5, or 2-4, or 2-3 combined mutations in the two IgA heavy chains.

3. CrossMab Technique

As discussed above, the knobs-into-holes technology or charge swapping enables heterodimerization of the antibody heavy chains. Correct association of the light chains and their cognate heavy chains can be achieved by exchange of heavy-chain and light-chain domains within the antigen binding fragment (Fab) of one half of the bispecific antibody binding unit.

Crossover can occur as a crossover of the complete VH-CH and VL-CL domains, crossover of only the VH and VL domains. or the CA and CL domains within the one half of the bispecific binding unit of an IgA antibody. This "crossover" retains the antigen-binding affinity but makes the two arms so different that light-chain mispairing can no longer occur. For further details, in the context of IgG antibodies, see, for example, Schaeffer et al., (2011) *Proc Natl Acad Sci USA* 108(27): 11187-11192.

4. Production of Multi-Specific IgA Binding Molecules

The coding sequences of the heavy chains of the bispecific IgA antibody binding units, with the desired mutations (following the knobs-into-holes, charge swap and/or Cross-Mab technique) may be produced by introducing appropriate nucleotide changes into the antibody DNA, or by nucleotide synthesis. The antibodies can then be produced by recombinant means.

Methods for recombinant production are widely known in the state of the art and comprise protein expression in prokaryotic and eukaryotic cells with subsequent isolation of the antibody and usually purification to a pharmaceutically acceptable purity. For the expression of the antibodies in a host cell, nucleic acids encoding the respective modified heavy chains, and optionally light chains, are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the antibody is recovered from the cells (supernatant or cells after lysis). General methods for recombinant production of antibodies are described, for example, in the review articles of Makrides, S. C., *Protein Expr. Purif* 17 (1999) 183-202; Geisse, S., et al., *Protein Expr. Purif* 8 (1996) 271-282; Kaufman, R. J. *Mol. Biotechnol.* 16 (2000) 151-161; Werner, R. G., *Drug Res.* 48 (1998) 870-880.

The bispecific antibodies are suitably separated from the culture medium by conventional immunoglobulin purification procedures such as, for example, protein A-SEPHAROSE®, hydroxyapatite chromatography, gel electrophoresis, dialysis, or affinity chromatography.

The methods of the present invention will result in a composition comprising a bispecific IgA binding molecule, such as a bispecific IgA antibody, as the main component, in combination with various by-products of the manufacturing process, such as monospecific antibodies, antibody fragments, monomers, dimers, trimers, and/or tetramers of the bispecific binding unit, instead of the desired pentameric or hexameric structure. The compositions produced will generally contain at least about 70%, or at least about 75%, or at least about 80%, or at least about 85%, or at least about 90%, or at least about 92%, or at least about 95%, of the desired penta- or hexameric bispecific binding molecule, e.g. antibody, which will be further purified by methods known in the art to yield a product with a purity of at least about 90%, or at least about 95%, or at least about 98%, or at least about 99%, or at least about 99.5%, or at least about 99.9%.

Multi-specific IgA antibodies and other multi-specific, such as bispecific, binding molecules can be produced in analogous fashion.

5. Applications of the Multi-Specific IgA Binding Molecules

The multi-specific, such as bispecific IgA binding molecules, e.g. antibodies of the present invention have widespread therapeutic and diagnostic applications.

IgA constitutes a large component of the humoral immune system of the body and protective functions at mucosal surfaces, playing an important role in maintenance of mucosal immunity. IgA, in the form of dimers and higher oligomers, is efficiently transported across cell membranes and released into external secretions where it forms the first specific immunologic defense against infection. IgA has been shown to fight bacterial infections by a variety of mechanisms, including direct killing, agglutination, inhibition of epithelial attachment and invasion, inactivation of enzymes and toxins, opsonization, and complement activation. IgA in secretions also protects against viral diseases targeting mucosal surfaces. For further details see, e.g. Mostow, K. E., *Annu. Rev. Immunol.* 1994, 12:63-84.

Thus, the multi-specific IgA antibodies of the present invention are uniquely suited for the treatment of microbial, e.g. bacterial, viral or fungal infections.

Examples of microbial infections include, without limitation, bacterial infections, e.g. *Clostridium difficile* (*C. difficile*) infection or multidrug resistant *S. aureus* infection, fungal infections, e.g. infections caused by *Candida albicans* or an *Aspergillus* species. Examples of viral infections include, without limitation, infection by respiratory viruses, e.g. influenza virus infections (flu), and infections by the respiratory syncytial virus (RSV).

The multi-specific IgA binding molecules, such as multi-specific IgA antibodies, e.g. dimeric bispecific IgA antibodies of the present invention can additionally be used to treat infections by Varicella-Zoster Virus, Adenoviruses, Human Immunodeficiency Virus, Human Metapneumovirus, West Nile Virus, the virus causing Severe Acute Respiratory Syndrome (SARS), and the like. The multi-specific IgA binding molecules, such as multi-specific IgA antibodies, e.g. dimeric bispecific IgA antibodies of the present invention can also be used to treat against strains of further bacteria such as *Bacillus anthracis, Clostridium botulinum* toxin, *Clostridium perfringens* epsilon toxin *Yersinia Pestis, Francisella tularensis, Coxiell burnetii, Brucella* species, *Staphylococcus enteroloxin* B.

In a preferred embodiment, the multi-specific IgA binding molecules, such as multi-specific IgA antibodies, e.g. dimeric bispecific IgA antibodies of the present invention are used for the treatment of *Clostridium difficile* infections. The *Clostridium difficile* is a spore forming gram positive bacterium that is normally a minor component of the microbiome in the human gut. However, in seniors, infants or immune compromised individuals undergoing antibiotic treatment, *C. difficile* can become fulminant leading to severe diarrhea, colitis and death. Management of *C. difficile* infections involves cessation of the initial antibiotic and treatment with metronidazole, vancomycin or fidaxomycin. Initial treatment is often successful, but patients have a 30% rate of either incomplete response to treatment or recurrence of infection. Thus, there is a major need for more effective treatment modalities.

The pathogenesis of *C. difficile* is predominantly due to two toxins secreted by the organism in the gut: toxin A and toxin B. The toxins are similar in structure and both cause cell rounding, detachment, and cell death by deglycosylating critical GTPases required for maintaining cytoskeletal structure. Monoclonal antibodies have been identified that potently neutralize toxin A and toxin B and these antibodies have shown promise in treatment of *C. difficile* infections in both animal models and human clinical trials. In the animal studies, individual monoclonal antibodies that neutralized either toxin A or toxin B could not inhibit *C. difficile* toxin mediated toxicity, while a cocktail of both antibodies provides significant protection. Bispecific IgA antibodies specifically targeting toxin A and toxin B will provide significant additional benefits, due to the unique properties of IgA.

In another preferred embodiment, the multi-specific IgA binding molecules, such as multi-specific IgA antibodies, e.g. dimeric bispecific IgA antibodies of the present invention are used for the treatment of human respiratory cyncytical virus (RSV) infections. RSV is a ubiquitous respiratory virus that causes serious lower respiratory tract disease and is the leading cause of pneumonia and bronchiolitis in infants and the elderly. The two major glycoproteins on the surface of the respiratory syncytial virus (RSV) virion, the attachment glycoprotein (G) and the fusion glycoprotein (F), control the initial phases of infection. G targets the ciliated cells of the airways, and F causes the virion membrane to fuse with the target cell membrane. Antibodies to protein F are described, for example, in U.S. Pat. Nos. 5,824,307 and 6,818,216. Antibodies to protein G are described, for example, in U.S. Pat. No. 7,736,648. The bispecific IgA dimers of the present invention provide significant additional benefits, due to the unique properties of IgA, including its ability to be effectively delivered to the lung.

In a further preferred embodiment, the multi-specific IgA binding molecules, such as multi-specific IgA antibodies, e.g. dimeric bispecific IgA antibodies of the present invention are used for the treatment of infections caused by influenza viruses. Influenza infection (also referred to as "influenza" or "the flu") is one of the most common diseases in humans and domestic animals. Three types of influenza virus (types A, B and C) cause disease. Influenza virus surface glycoproteins bemagglutinin (HA) and neuraminidase (NA) exhibit extensive antigenic variability, and are the basis for classifying influenza subtypes. HA appears on the surface of virion envelopes, and is involved in viral entry into cells. HA is a transmembrane protein that is initially synthesized as a single polypeptide chain (HA0) of about 560 amino acids, which is subsequently proteolytically cleaved to form two subunits, HA1 and HA2. The subunits remain connected through disulfide bonds, and the protein appears on the surface of virions and infected cells as a homotrimer. R A Lamb, R M Krug, *Orthomyxoviridae*: the viruses and their replication. (See, D M Knipe, P M Howley, D E Griffin (Eds.) et al., *Fields Virology*, 4th edn., Lippincott Williams & Wilkins, 2001, pgs. 1487-1531). HA1 forms the globular head region of HA, and is responsible for most of the antigenic variability among HA subtypes. HA1 interacts with viral receptors on host cells. HA2 forms the fibrous stem of the viral spike, and is thought to be involved in fusion between the virion envelope and the host cell membrane. The stem region is more conserved among various different HA subtypes. (See, e.g., Wilson et al., Nature, 289:366-373, 1981; Skehel et al., Ann. Rev. Biochem., 69:531-569, 2000).

The antigenic variability of influenza viruses circulating in humans varies from year to year, and thus annual vaccination is required, with seasonal vaccines prepared based on predictions of the most prevalent subtypes in a given year. Unfortunately, the predictions are not always correct. Moreover, pandemic strains of influenza virus periodically jump from animal reservoirs into the human population. Such pandemic strains, e.g., H5N1, could cause severe disease spread without careful control. Thus there remains a need in the art for additional therapies to control influenza virus disease and spread.

As an alternative approach, antibody-based therapies that can prevent influenza infection or treat an existing infection through viral neutralization are in development. The primary target of most neutralizing antibodies that protect against influenza virus infection is the globular head region of HA, but the antigenic variability of this region poses challenges. Recently, broadly cross-neutralizing antibodies that recognize the conserved stem region of HA of influenza A and B viruses have been identified, although efficacy in clinical studies has not been demonstrated. (See, e.g., WO2008/028946, WO 2010/130636, and US20140120113A1). Polyclonal mixtures of IgA backbones have been shown to have enhanced neutralizing potency against influenza virus (He, W. et al., J. Virol. Doi: 10. 1128/JVI.03099-14, accepted manuscript posted online on Jan. 14, 2015).

Bispecific and multi-specific IgA binding molecules, such as multi- or bispecific dimeric antibodies of the present invention can be designed to target different antigens on various influenza viruses and influenza virus subtypes, and thus provide effective tools for the management of flu.

The multi-specific IgA binding molecules, such as IgA antibodies, of the present invention have many further wide-ranging applications.

In one embodiment, the multi-specific IgA binding molecules, e.g. antibodies herein bind to two or more sites on the same soluble target, such as, for example, VEGF, TNFα, or IL6. The purpose may, for example, be antagonizing multiple sites on the protein and/or increasing the avidity to a given target.

In another embodiment, the multi-specific IgA binding molecules, e.g. antibodies herein bind two or more sites on the same cell surface (receptor) target, such as EGFR or HER2 (ErbB2). Thus, for example, a bispecific binding molecule might target both the 4D5 and the 2C4 epitopes on a HER2 molecule. This approach may increase bio-potency and/or avidity to a given target.

In yet another embodiment, the multi-specific IgA binding molecules, e.g. antibodies of the present invention bind two or more different soluble targets (globular proteins or peptides), e.g. TNFα and IL6, VEGFα and Ang2, or two cytokines. This approach might result in more complete blocking a specific pathway; blocking of the so called "cytokine storm," or coordinate an enzyme and its substrate, e.g. Factor IXa and Factor X.

In a further embodiment, the multi-specific IgA binding molecules, e.g. antibodies herein may bind one or more soluble targets and one or more cell surface receptor targets, such as an angiogenic factor and neo-vascular specific receptor. The purpose of this approach may also be increased delivery and blockade at specific sites or tissues.

In a still further embodiment, the multi-specific IgA binding molecules, e.g. antibodies herein are designed to bind two or more different cell surface receptor targets, such as, for example, HER2 (ErbB2) and HER3 (ErbB3). This may result in enhancing specificity and selectivity and/or in more complete blocking of a given pathway.

The multi-specific IgA binding molecules, e.g. antibodies of the present invention may also be designed to bind one soluble target or cell surface receptor target and a long residence time target, such as, for example, TNFα and serum albumin, or VEGF and serum albumin. These molecules are expected to have longer circulating half-life than binding molecules without the albumin specificity.

In a further embodiment, the multi-specific IgA binding molecules, e.g. antibodies herein may bind one or more soluble targets and one or more matrix proteins or substrates, such as, for example, VEGFα and hyaluronic acid. The resultant bispecific binding molecules may find utility, for example, in anti-angiogenic therapy of ocular conditions, such as age-related macular degeneration (AMD), due to their increased residence time in the intraocular space.

Bispecific IgA binding molecules, e.g. antibodies binding one soluble or receptor target, plus a transporter receptor (ie transferrin receptor), e.g. anti-EGFRvIII (mutant form with exon III deleted) found glioblastoma combined with anti-transferrin specificity, can find utility in antibody delivery across blood brain barrier.

Other multi-specific IgA binding molecules, e.g. antibodies may bind two or more different cell types, such as B and T cells. Such antibodies may find utility, for example, in B and/or T cell related diseases or conditions, such as rheumatoid arthritis (RA) or non-Hodgkin's lymphoma.

In all embodiments, the use of dimeric bispecific IgA antibodies is preferred.

Pharmaceutical compositions comprising an effective amount of multi-specific IgA-binding molecules, such as multi-specific IgA antibodies, e.g. bispecific dimeric IgA antibodies for the treatment of any and all above-mentioned and related conditions, associated with the target antigens are expressly within the scope of the present invention, along with methods and uses for the treatment of such conditions.

6. Compositions, Pharmaceutical Compositions, and Methods of Treatment

In one aspect, the invention concerns compositions comprising purified multi-specific IgA antibodies herein. The compositions generally will contain at least about 80%, or at least about 85%, or at least about 90%, or at least about 92%, or at least about 95%, or at least about 98%, or at least about 99% of the desired bispecific IgA binding molecule, e.g. antibody. The composition may be a pharmaceutical composition, where the bispecific binding molecule, e.g. antibody, is in admixture with at least one pharmaceutically acceptable carrier.

In various embodiments, the pharmaceutical compositions of the present invention comprise an effective amount of a multi-specific IgA binding molecule, such as a multi-specific IgA antibody, e.g. a dimeric bispecific IgA antibody of the present invention for the treatment of a condition or disease listed above. In all embodiments, the use of dimeric bispecific IgA antibodies is preferred.

A pharmaceutical composition of the present invention can be administered by a variety of methods known in the art. As will be appreciated by the skilled artisan, the route and/or mode of administration will vary depending upon the target disease or condition and the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The compositions may also contain adjuvants such as preservatives, wetting agents, emulsifying agents and/or dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

All publications mentioned herein are expressly incorporated herein by reference in their entirety to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

The following examples, sequence listing and figures are provided to aid the understanding of the present invention, the true scope of which is set forth in the appended claims. It is understood that modifications can be made in the procedures set forth without departing from the spirit of the invention.

Example 1

1. Generation of DNA Constructs with Designed Mutations a. Materials and Methods:Generate DNA constructs with designed mutations b. DNA construct synthesis All the DNA constructs with designed mutations are synthesized by the commercial vendors (Genescript), with compatible restriction sites at both ends for subcloning into respective expression vectors.

C. Constructing expression vectors

The synthesized DNA constructs are re-suspended in Tris-EDTA buffer at 1 µg/ml. DNA (1 µg) is subjected to enzyme digestion and the synthesized gene is separated from the carrier plasmid DNA by electrophoresis. The digested DNA is ligated to pre-digested plasmid DNA (pFUSEss-CHIg-hA1 for a chain, pFUSE2ss-CLIg-hk for kappa chain, Invivogen) by standard molecular biology techniques. The ligated DNA is transformed into competent bacteria and plated on LB plates with multiple selective antibiotics. Several bacterial colonies are picked and DNA preparations are made by standard molecular biology techniques. The prepared DNA are verified by sequencing. Only the bacterial clones with 100% match of DNA sequence with the designed DNA sequence are used for plasmid DNA preparation and subsequently for cell transfection.

d. Different size of α chains

In order to demonstrate that two different alpha chains (A and B) will be able to couple together, two different alpha chains are constructed with distinct molecular weights and ligand specificities.

e. The A chain is composed of a full length α chain for chimeric OKT3 (anti-CD3) VH region fused with CA1 of human alpha chain:

(SEQ ID NO: 23)
QVQLQQSGAELARPGASVKMSCKASGYTFTRYTMHWVKQRPGQGLEW

IGYINPSRGYTNYNQKFKDKATLTTDKSSSTAYMQLSSLTSEDSAVY

YCARYYDDHYCLDYWGQGTTLTVSSASPTSPKVFPLSLCSTQPDGNV

VIACLVQGFFPQEPLSVTWSESGQGVTARNFPPSQDASGDLYTTSSQ

LTLPATQCLAGKSVTCHVKHYTNPSQDVTVPCPVPSTPPTPSPSTPP

TPSPSCCHPRLSLHRPALEDLLLGSEANLTCTLTGLRDASGVTFTWT

PSSGKSAVQGPPERDLCGCYSVSSVLPGCAEPWNHGKTFTCTAAYPE

SKTPLTATLSKSGNTFRPEVHLLPPPSEELALNELVTLTCLARGFSP

KDVLVRWLQGSQELPREKYLTWASRQEPSQGTTTFAVTSILRVAAED

WKKGDTFSCMVGHEALPLAFTQKTIDRLAGKPTHVNVSVVMAEVDGT

CY

The A chain has a molecular weight about 55 kD and able to bind to soluble epsilon chain of CD3 (10977-H08H, Sino Biological), or T cells.

f. The B chain has a cMyc tag fused with the (Gly4Ser)-hinge-CA2-CA3 of human α chain:

(SEQ ID NO: 24)
GEQKLISEEDLGGGGSTPPTPSPSTPPTPSPSCCHPRLSLHRPALED

LLLGSEANLTCTLTGLRDASGVTFTWTPSSGKSAVQGPPERDLOGCY

SVSSVLPGCAEPWNHGKTFTCTAAYPESKTPLTATLSKSGNTFRPEV

HLLPPPSEELALNELVTLTCLARGFSPKDVLVRWLQGSOELPREKYL

TWASRQEPSOGTTTFAVTSILRVAAEDWKKGDTFSCMVGHEALPLAF

TQKTIDRLAGKPTHVNVSVVMAEVDGTCY

The B chain has a molecular weight about 28 kD and is able to bind to anti-myc monoclonal antibody 9E4 or other anti-myc antibodies.

g. The alternative B chain has a full length α chain for CrossMab$^{VH-CL}$ (V$_H$+C$_L$) Rituximab (anti-CD20) fused with hinge-CA2 of human alpha chain:

(SEQ ID NO: 25)
QVQLQQPGAELVKPGASVKMSCKASGYTFTSYNMHWVKQTPGRGLEW

IGAIYPGNGDTSYNQKFKGKATLTADKSSSTAYMQLSSLTSEDSAVY

YCARSTYYGGDWYFNVWGAGTTVTVSASVAAPSVFIFPPSDEQLKSG

TASVVCLLNNFYPREAKVQWKVDNALQSGNSQESVTEQDSKDSTYSL

SSTLTLSKADYEKHKVYACEVTHQGLSSPVTKSFNRGECPVPSTPPT

PSPSTPPTPSPSCCHPRLSLHRPAIEDLLLGSEANLTCTLTGLRDAS

GVTFTWTPSSGKSAVQGPPERDLCGCYSVSSVLPGCAEPWNHGKTFT

CTAAYPESKTPLTATLSKSGNTFRPEVHLLPPPSEELALNELVTLTC

LARGESPKDVLVRWLQGSQELPREKYLTWASRQEPSQGTTTFAVTSI

LRVAAEDWKKGDTFSCMVGHEALPLAFTQKTIDRLAGKPTHVNVSVV

MAEVDGTCY

The B chain has a molecular weight about 55 kD and is able to bind to CD20 positive B cells.

h. Different light chain coupling P-24,DNA
i. Native chimeric OKT3 kappa chain (SEQ ID NO: 26)
QIVLTQSPAIMSASPGEKVTMTCSASSSVSYMNWYQQKSGTSPKRWI

YDTSKLASGVPAHFRGSGSGTSYSLTISGMEAEDAATYYCQQWSSNP

FTFGSGTKLEINRAVAAPSVFIFPPSDEQLKSGTAVVWCLLNNFYPR

EAKVQWKVDNALQSGNSQESVTEQDSKDSTYSLSSTLTLSKADYEKH

KVYACEVTHQGLSSPVTKSFNRGEC j. CrossMabL$^{VL-CH1}$ for Rituximab (SEQ ID NO: 27)
QIVLSQSPAILSASPGEKVTMTCRASSSVSYIHWFQQKPGSSPKPWI

YATSNLASOVPVRFSGSGSGTSYSLTISRVEAEDAATYYCQQWTSNT

PTFGSGTKLEIKSSASTKGPSVFPLAPSSKSTSGGTAALGCLVKDYF

PEPVTVSWNSGALTSGVHTFPAVLQSSGLYSLSSVVTVPSSSLGTQT

YIONVNHKPSNTKVDKRVEPKSO

The light chains have a molecular weight about 25 kD.

k. Different selection markers for different expression vectors

Different selection markers are used on different expression vectors used for co-transfection. Multiple drugs are used for selection of cells in order to accommodate all necessary expression vectors relevant for IgA production. Standard molecular biology techniques are used for cloning specific DNAs into these vectors.

l. Alpha chain utilizes Zeocin selection (ant-zn-1, Invivogen). Zeocin is used at a concentration of 100 μg/ml. After transfection with a plasmid containing the Sh ble gene, then the cells are incubated in Opti-CHO medium containing Zeocin at 100 μg/ml to select for stable transfectants.

m. Kappa chain utilizes Blasticidin S selection (ant-bl-1, Invivogen). Blasticidin S is used at a concentration of 10 μg/ml. After transfection with a plasmid containing the bsr gene, then the cells are incubated in Opti-CHO medium containing Blasticidin S at 10 μg/ml to select for stable transfectants.

n. Protein expression, purification and characterization
o. Transfection
p. IgA is made by co-transfection of several different expression vectors at equal molar ratios or variable molar ratio (5 to 10 fold difference) into mammalian cells, such as 293 cells or CHO cells. DNA for expression vectors are mixed with PEI and then added to CHO-S cells. PEI transfection with CHO-S cells is conducted according to established techniques (see "Biotechnology and Bioengineering, Vol 87, 553-545").
q. Protein purification
r. Jacalin-Agarose (Catalog # gel-jac-5, Invivogen)
IgA proteins from transfected CHO-S cell supernatants are purified by affinity Jacalin-Agarose according to manufacturers' protocol.
S. Capto-L (Catalog 17-5478-01, GE Healthcare)
Transfected IgA protein, containing kappa chain, in CHO-S cell supernatant is purified by Capto-L affinity matrix according to manufacturers' protocol.
t. Gel electrophoresis
u. Non-reducing SDS PAGE
v. Non-reducing SDS PAGE separates native IgA and its engineered forms according to size. IgA, composed of homodimeric heavy chains (AA) with their light chains, produces a protein band of approximately 160 kDa molecular weight. Homodimeric IgA composed of a shorter version of homodimeric heavy chains (BB), for example with cMyc-tagged-IgA-Fc, produces a protein band of significantly lower molecular weight. IgA composed of heterodimeric heavy chains (AB) produce multiple proteins with molecular weights greater than BB and less than AA.
w. NuPage LDS Sample Buffer (Life Technologies) is added to IgA protein samples at 25° C. for 30 minutes before loading onto the gel. NativePage Novex 3-12% Bis-Tris Gel (Life Technologies) is used with Novex Tris-Acetate SDS Running Buffer (Life Technologies). Run gel until the dye front reaches the bottom of the gel.
x. Reducing SDS-PAGE
y. NuPage LDS sample buffer (Life Technologies) and NuPage reducing agent dithiothreitol (Life Technologies) are added to IgA protein samples and heated to 80° C. for 10 minutes before loading on NuPage Novex 4-12% Bis-Tris Gel (Life Technologies, cat# NP0322). NuPage MES SDS Running Buffer (Life Technologies, cat# NP0002) is used for gel electrophoresis. Gels are run until the dye front reaches the bottom of the gel.

z. After electrophoresis is complete, remove gel from apparatus and stain the gel using Colloidal Blue Staining (Life Technologies, manual #LC6025)

aa. Gel band quantitation

Protein gels are dried, then digitized using image scanner. The gel image is processed with Image J program and the amount of protein in a specific band can be determined using the gel quantitation function bb. Mass spectrometric analysis to identify/quantify the various mAbs in the bi-specific preparation.

cc. Stability analysis using differential scanning calorimetry (DSC)

dd. Bispecific functional analysis ee. ELISA analysis for two ligands

IgA with OKT3 (chain A) and cMyc peptide (chain B) is assayed by ELISA analysis with soluble CD3epsilon protein capture and anti-cMyc (9E10) detection. Soluble CD3epsilon protein is coated on ELISA plate at 2 mg/ml in 150 mM NaHCO$_3$ followed by blocking with 3% BSA in PBS. Supernatant (100 µl) containing transfected IgA-OKT3-cMyc is added to blocked ELISA plate for 4 hours at 25° C. After washing with PBS, the 9E10 antibody is added to the ELISA plate for 2 hours at room temperature. Anti-mouse IgG-HRP is added following washes with PBS. The existence of bispecific IgA is detected by reading at OD 450 after adding HRP substrate.

ff. FACS analysis of target binding

IgA-OKT3-cMyc binding to T cell is confirmed by binding of antibody to T cell line (Peer, positive cell line) and B cell line (Daudi, negative control cell line).

After washing, rhodamine-labeled 9E10 is added to the cell suspension. The cell target binding is detected by MFI of both positive and negative controlled cells with or without CD3 antigen.

gg. Fluorescent microscopy assay for bispecific binding

Verify bispecific binding of the designed CD3×CD20 bispecific IgA by its ability to bring together two populations of CD3-positive cells and CD20-positive cells which have been pre-labeled by two different vital dyes on each cell type. For example:

hh. Green Fluorescent cytosolic vital dye (CellTrace™ Calcein Green AM) labeling for CD3-positive cell line (Jurkat)

ii. Red Fluorescent cytosolic vital dye (CellTrace™ Calcein Red-Orange, AM) labeled CD20-positive B-cell cell line (Daudi)

Example 2

Trafficking of Bispecific Dimeric IgA to the Lung

The ability of bispecific, dimeric IgA to be delivered to the lung can be investigated by a variety of methods. For example, groups of 3-4 week old female BALB/c mice are injected IV with human IgG1/kappa or dimeric IgA/kappa in PBS at doses up to 50 mg/kg. Alternatively, human or mouse anti-CD20 antibodies may be used. At 4 hrs post injection, blood samples are collected and processed for plasma. Immediately prior to sacrifice, the mice are anesthetized and exsanguinated. Following the removal of cervical lymph nodes, nasal wash samples are collected by exposing the trachea and washing the upper trachea and nasal cavity with 200 µL of PBS. Bronchoalveolar lavage (BAL) samples are collected by inserting catheters into the trachea and washing the lungs three times with 1 mL PBS (3 mL total, clarified by centrifugation). The protease inhibitor phenylmethylsulfonyl fluoride is added to all samples at a concentration of 1 mM following collection, and all samples are stored at or below −20° C. until analysis.

The concentration of test antibody in each sample is assayed by ELISA. Briefly, goat polyclonal anti-human kappa light chain antibody that has been cross-absorbed with mouse Ig is coated onto the wells of 96-well ELISA plates overnight at 4 C and then unreacted sites are blocked with PBS containing 3% bovine serum albumin. Alternatively, the plates may be coated with a soluble form of human CD20. After washing, serially-diluted test samples and standards are applied to the plates and incubated for 1 hr at 37 C. The plates are then washed with PBS containing 0.05% Tween 20 and incubated with alkaline phosphatase-conjugated heavy-chain-specific goat anti-human IgG or IgA that has been cross-absorbed against mouse Ig. For mouse test antibodies, immobilized CD20 would be used for capture and alkaline phosphatase-conjugated heavy-chain-specific goat anti-mouse IgG or IgA would be used for detection. The plates are developed with p-nitrophenyl phosphate and read at an optical density (OD) of 405 nm. Based on results from the IgA and IgG standard curves, the concentration of test antibody in each sample is calculated.

Example 3

Bispecific Dimeric IgA Antibodies to RSV F and G Antigens

Human respiratory syncytial virus (RSV) is a ubiquitous respiratory virus that causes serious lower respiratory tract disease and is the leading cause of pneumonia and bronchiolitis in infants and the elderly. The two major glycoproteins on the surface of the respiratory syncytial virus (RSV) virion, the attachment glycoprotein (G) and the fusion glycoprotein (F), control the initial phases of infection. G targets the ciliated cells of the airways, and F causes the virion membrane to fuse with the target cell membrane.

According to the present Example, a unique dimeric IgA molecule is engineered, consisting of one heavy and light chain combination with sequences that can bind to the RSV F protein and another heavy and light chain combination with sequences that can bind to the RSV G protein. Expression of these antibodies, using the technology described Example 1, will result in a single IgA molecule with two binding moieties for RSV F and two binding moieties for RSV G.

The heavy chain variable region sequence of an RSV G-binding moiety of a bispecific human anti-RSV IgA2 antibody, containing a Set #1, Knob, CA3 #1 mutation (bolded) as listed in Table 1, is shown as SEQ ID NO: 10. The human kappa light chain variable region sequence of the RSV G protein-binding moiety is shown as SEQ ID NO: 11.

The CrossMab version of the variable light region sequence of the anti-RSV F protein-binding moiety of the bispecific antibody fused to an engineered IgA2 antibody heavy chain (SEQ ID NO: 8), containing a Set #1, Hole, CA3 #2, CA1 mutation, is shown as SEQ ID NO: 12. The CrossMab version of the variable heavy region sequence of the anti-RSV F protein-binding moiety fused to an engineered kappa constant light domain (SEQ ID NO: 9) is shown as SEQ ID NO: 13.

The binding of a bispecific anti-RSV IgA antibody, with binding specificities to the RSV G and RSV F antigens is evaluated essentially as described in Example 1.ee, except that the reagents are modified depending upon the specific antigens and the nature of the bispecific antibody. For example, in an ELISA to evaluate an RSV bispecific IgA antibody that binds F-protein and G-protein, RSV F-protein (or an appropriate fragment thereof) is immobilized and used for ELISA capture whereas biotinylated soluble RSV G-protein (or an appropriate fragment thereof) is used for detection. Alternatively, the G-protein may be used for capture and soluble biotinylated F-protein may be used for detection. The existence of a bispecific IgA is detected by reading at OD 450 nm after adding Avidin-HRP and substrate.

The cultivation of RSV and in vitro RSV virus neutralization assays may be conducted using a variety of standard techniques, such as those described in U.S. Pat. No. 7,736,648. Briefly, HEp2 cells are plated in 12-well plates at $2 \times 10^5$ cells/well. The following day, serial dilutions of antibodies are generated in media. Approximately 200 PFU/well of RSV is added to the antibodies in the presence of rabbit complement serum and incubated for one hour at room temperature. The antibody-virus mixture is then added to HEp2 cells at 200 uL/well and incubated for 2 hr at room temperature to allow for infection. Following this infection period, media is removed and media containing 1% methyl cellulose is added to all wells. Plates are incubated at 35 degrees C. for 6 days, after which time, cells are fixed and stained for plaque number determination as follows: Methyl cellulose is aspirated from the cell layers, and cells are fixed in 100% methanol for 30 min at room temperature. The plates are then washed 3 times with 5% milk in PBS. Primary antibody is added at 1:500 dilution (Goat anti-RSV polyclonal antibody (Chemicon Cat#AB1128)) in PBS+5% Milk Protein for 1 hr. Plates are washed again 3 times with 5% milk in PBS. Secondary antibody is then added at 1:500 dilution in 5% milk protein in PBS (ImmunoPure Rabbit anti-goat antibody IgG (H+L) Peroxidase conjugated) (Thermo Scientific, Cat#31402)) for 1 hr. Plates are washed 3.times with 1xPBS. Plaques are visualized by adding 1-Step Chloronaphthol substrate (Pierce, Cat#34012), 200 uL per well for 10 min. Plates are rinsed with water and allowed to air dry. Plaques are counted in each well by manual inspection.

In vivo RSV neutralization studies may be conducted using a variety of standard techniques, such as the mouse prophylaxis studies described in Collarini et al 2009 (J. Immunol. 183_6338-6345). Briefly, groups of female BALB/c mice, 6-8 wk old, are injected with the antibodies to be tested (bispecific IgA antibodies as well as positive and negative controls) at doses up to 50 mg/kg. Twenty-four hours later (prophylaxis model), the mice are infected intranasally with $10^6$ PFU of RSV Long strain virus. Alternatively, antibody may be administered up to several days after the viral challenge (treatment model). After 5 days, the animals are sacrificed and their lungs excised. Viral load is quantified on day 5 by (i) PFU per gram of lung tissue, or (ii) quantitative PCR after extracting RNA from lung tissue using a Trizol extraction kit (Invitrogen). Virus N-gene copy number is expressed as a percent of the actin mRNA content of the tissue sample. Control animals either do not receive any anti-RSV mAb or receive a non-immune isotype control mAb.

Example 4

Bispecific Dimeric IgA Antibodies to Influenza Antigens

Influenza infection (also referred to as "influenza" or "the flu") is one of the most common diseases in humans and domestic animals. Three types of influenza virus (types A, B and C) cause disease. Influenza virus surface glycoproteins hemagglutinin (HA) and neuraminidase (NA) exhibit extensive antigenic variability, and are the basis for classifying influenza subtypes. HA appears on the surface of virion envelopes, and is involved in viral entry into cells. HA is a transmembrane protein that is initially synthesized as a single polypeptide chain (HA0) of about 560 amino acids, which is subsequently proteolytically cleaved to form two subunits, HA1 and HA2. The subunits remain connected through disulfide bonds, and the protein appears on the surface of virions and infected cells as a homotrimer. R A Lamb, R M Krug, Orthomyxoviridae: the viruses and their replication. (See, D M Knipe, P M Howley, D E Griffin (Eds.) et al., Fields Virology, 4th edn., Lippincott Williams & Wilkins, 2001, pgs. 1487-1531). HA1 forms the globular head region of HA, and is responsible for most of the antigenic variability among HA subtypes. HA1 interacts with viral receptors on host cells. HA2 forms the fibrous stem of the viral spike, and is thought to be involved in fusion between the virion envelope and the host cell membrane.

According to the present Example, a unique dimeric IgA molecule is engineered, consisting of one heavy and light chain combination with sequences that can bind to two different antigens on the HA subunit of an influenza A virus. Expression of these antibodies, using the technology described Example 1, will result in a single IgA molecule with two binding moieties for each HA epitope. Alternatively, a bispecific IgA antibody directed to epitopes on HA and NA can be constructed.

The heavy chain variable region sequence of a first HA binding moiety of a bispecific human anti-influenza IgA antibody, containing a Set #1, Knob, CA3 #1 mutation (bolded) as listed in Table 1, is shown as SEQ ID NO: 14. The human kappa light chain variable region sequence of the associated with the heavy chain variable region is shown as SEQ ID NO: 15.

The CrossMab version of the variable light region sequence of a second HA binding moiety of the bispecific antibody fused to an engineered IgA2 antibody heavy chain (SEQ ID NO: 8), containing a Set #1, Hole, CA3 #2, CA1 mutation, is shown as SEQ ID NO: 16. The CrossMab version of the variable heavy region sequence of a second HA binding moiety fused to an engineered kappa constant light domain (SEQ ID NO: 9) is shown as SEQ ID NO: 17

The binding of a bispecific anti-influenza IgA antibody to two antigens is evaluated essentially as described in Example 1, except that the reagents are modified depending upon the specific antigens and the nature of the bispecific. For example, in an ELISA to evaluate a flu bispecific IgA that binds to HA and NA, one flu protein or peptide is immobilized and used for ELISA capture whereas a different flu protein or peptide is biotinylated and used for detection. The existence of a bispecific IgA is detected by reading at OD 450 nm after adding Avidin-HRP and substrate.

The cultivation of flu virus and in vitro flu virus neutralization assays may be conducted using a variety of standard techniques, such as those described in Throsby et al. 2008 (PLoS One 3,e3942). Briefly, MDCK cells are maintained in minimum essential medium (MEM) supplemented with 10% fetal calf serum (FCS) and 1% penicillin-streptomycin (PS) at 37° C. On the day of the experiment, MDCK cells in 96-well format are washed twice with PBS and incubated in MEM supplemented with 1% FCS, 1% PS and 1 mg/ml TPCK trypsin (for non-H5 viruses). Two-fold serially diluted antibodies are mixed with an equal volume of viral inoculum, followed by 2 hour incubation at 37° C. After the incubation, the mixture (~100 TCID50) is added to confluent MDCK monolayers. Cells are cultured for 72 hours before the examination of cytopathic effect (CPE). CPE is compared to the positive control (virus-inoculated cells) and negative controls (mock-inoculated cells). The absence of CPE in individual wells is defined as protection.

In vivo protection studies can be conducted using a variety of standard techniques, such as those described in Throsby et al. 2008 (PLoS One 3,e3942). Briefly, groups of female 7-week-old BALB/c mice are injected IP with the antibodies to be tested (bispecific IgA antibodies as well as positive and negative controls) at doses up to 50 mg/kg (prophylaxis model). Twenty-four hours later, the mice are inoculated intranasally with lethal doses of virus (typically 10× to 25× the LD50) and observed for 21 days. Alternatively, antibody may be administered up to several days after the viral challenge (treatment model). Clinical signs are scored with a scoring system (0=no clinical signs; 1=rough coat; 2=rough coat, less reactive, passive during handling; 3=rough coat, rolled up, laboured breathing, passive during handling; 4=rough coat, rolled up, laboured breathing, unresponsive) and recorded, as is survival. Body weights may also be monitored. Control animals typically die within 12 to 15 days post challenge.

Example 5

Bispecific Dimeric IgA Antibodies to *Clostridium difficile* Toxins A and B

As described earlier, *Clostridium difficile* is a spore forming gram positive bacterium that is normally a minor component of the microbiome in the human gut. However, in seniors, infants, or immune compromised individuals undergoing antibiotic treatment, *C. difficile* can become fulminant leading to severe diarrhea, colitis and death. Management of *C. difficile* infections involves cessation of the initial antibiotic and treatment with metronidazole, vancomycin or fidaxomycin. Initial treatment is often successful, but patients have a 30% rate of either incomplete response to treatment or recurrence of infection. Thus, there is a major need for more effective treatment modalities.

According to the present Example, a unique dimeric IgA molecule is engineered, consisting of one heavy and light chain combination with sequences that can bind and neutralize *C. difficile* toxin A and a second heavy and light chain combination designed to bind and neutralize toxin B. Expression of these antibodies using the technology described herein (see Example 1) will result in a single IgA molecule with two binding moieties for toxin A and two binding moieties for toxin B that can effectively traffic to the intestinal site of *C. difficile* infection upon systemic administration. Such a unique IgA molecule will have an improved dose response for treatment of *C. difficile* recurrent infections or will improve the effectiveness of initial treatment in subjects with life-threatening *C. difficile* disease.

The heavy chain variable region sequence of the Toxin A binding moiety of a bispecific human anti-*C. difficile* antibody, containing a Set #1, Knob, CA3 #1 mutation (bolded) as listed in Table 1, is shown as SEQ ID NO: 18. The human kappa light chain variable region sequence of the associated with the heavy chain variable region is shown as SEQ ID NO: 19.

The CrossMab version of the variable light region sequence of the toxin B binding moiety of the bispecific antibody fused to an engineered IgA2 antibody heavy chain (SEQ ID NO: 8), containing a Set #1, Hole, CA3 #2, CA1 mutation, is shown as SEQ ID NO: 20. The CrossMab version of the variable heavy region sequence of the toxin B binding moiety fused to an engineered kappa constant light domain (SEQ ID NO: 9) is shown as SEQ ID NO: 21.

The binding of a bispecific anti-*C. difficile* IgA antibody to two antigens is evaluated essentially as described in Example 1.ee, except that the reagents are modified depending upon the specific antigens and the nature of the bispecific. For example, in an ELISA to evaluate a bispecific IgA that binds to *C. difficile* toxin-A and toxin-B, Toxin-A (or an appropriate fragment thereof) is immobilized and used for ELISA capture whereas a biotinylated Toxin-B (or an appropriate fragment thereof) is used for detection. Alternatively, Toxin-B may be used for capture and soluble biotinylated Toxin-A may be used for detection. The existence of a bispecific IgA is detected by reading at OD 450 nm after adding Avidin-HRP and substrate.

In vitro *C. difficile* toxin-A and toxin-B toxin neutralization assays may be conducted using a variety of standard techniques, such as those described in Babcock et al. 2006 (Infect. Immun. 74, 6339-6347). Briefly, when IMR-90 lung fibroblast cells are incubated in the presence of varying concentrations of toxin-A or toxin-B, the cells round up and lose adherence to cell culture dishes. This cytopathic effect (CPE) is determined by visual inspection of cells and a CPE score from 0-4 is determined, based on the results of the visual inspection. To test for neutralization, IMR-90 cells are seeded at $1\times10^5$ cells per well in a 96-well microtiter plate and incubated for 12 h at 37° C. with 5% $CO_2$. Toxin A (6 ng/ml) or toxin B (20 μg/ml) is incubated with various concentrations of antibody for 1 h, added to the cell culture, and incubation is continued for 18 h at 37° C. Cytopathic effect is then determined microscopically and scored as 0 (0% rounded cells), 1 (25% rounded cells), 2 (50% rounded cells), 3 (75% rounded cells), or 4 (100% rounded cells) and the results are plotted as CPE vs antibody dose. From the titration curves, an IC50 for the antibody can be calculated.

The cultivation of *C. difficile* and in vivo *C. difficile* toxin-A and toxin-B neutralization assays can be conducted using a variety of standard techniques, such as the hamster protection models described by Babcock et al. 2006 (Infect. Immun. 74, 6339-6347). For protection against *C. difficile*-induced lethality, groups of Syrian golden hamsters (70 to 80 g) are given four total doses of antibody intraperitoneally (bispecific IgA antibodies as well as positive and negative controls) for 4 days beginning 3 days prior to the administration of *C. difficile* spores. Clindamycin (10 mg/kg) is administered intraperitoneally 24 h prior to *C. difficile* spore challenge, and the hamsters are then challenged with 140 B1 spores orogastrically using a standard small animal feeding needle. Control animals typically die within 72 hrs post challenge.

The invention claimed is:

1. A dimeric bispecific IgA antibody comprising two binding units in end-to-end configuration and a J-chain, wherein each binding unit is bispecific, each having the same two binding specificities, AB, AB, wherein each binding unit comprises two IgA heavy chain constant region sequences each comprising at least a CA3 domain, two light chain constant region sequences, two heavy chain variable region ($V_H$) sequences, and two light chain variable region ($V_L$) sequences, wherein the $V_H$ and $V_L$ combine to form two $V_H V_L$ antigen-binding regions each binding to a different epitope, wherein an asymmetric interface exists between the two IgA heavy chain constant regions in each binding unit via a knob-into-hole modification comprising:

(a) (i) a knob modification comprising a substitution of L220 with M and T236 with W; and
   (ii) a hole modification comprising:
      (1) a substitution of L220 with K, R, or W;
      (2) a substitution of T236 with G; and/or
      (3) a substitution of T282 with I, V, or L;

(b) (i) a knob modification comprising a substitution of L220 with M, H, F, or Y, T236 with F, and T282 with G; and
   (ii) a hole modification comprising:
      (1) a substitution of L220 with K, R, or W;
      (2) a substitution of T236 with V or I; and/or
      (3) a substitution of T282 with V;

(c) (i) a knob modification comprising a substitution of L220 with M, T236 with Y, and T282 with G; and
   (ii) a hole modification comprising:
      (1) a substitution of L220 with K, R, or W; and/or
      (2) a substitution of T236 with V;

(d) (i) a knob modification comprising a substitution of L220 with F, Y, or M, T236 with S, L238 with F, and T282 with S; and
   (ii) a hole modification comprising:
      (1) a substitution of L220 with K, R, or W; and/or
      (2) a substitution of T236 with S;

(e) (i) a knob modification comprising a substitution of L220 with W; and
(ii) a hole modification comprising:
(1) a substitution of L220 with K or R; and/or
(2) a substitution of T236 with G; or
(f) (i) a knob modification comprising a substitution of T234 with S and I284 with F or W; and
(ii) a hole modification comprising:
(1) a substitution of L220 with K, R, or W;
(2) a substitution of L238 with G or A;
(3) a substitution of A280 with M; and/or
(4) a substitution of T282 with S;
wherein the amino acid numbering corresponds to SEQ ID NO: 2.

2. The dimeric bispecific IgA antibody of claim 1, wherein the asymmetric interface between the two IgA heavy chain constant regions in each binding unit further comprises a salt-bridge charge modification, wherein the salt-bridge charge modification comprises:
(A) one of the two IgA heavy chain constant regions comprising a substitution of H218 with D or E and the other of the two IgA heavy chain constant regions comprising a substitution of E225 with K or R; or
(B) one of the two IgA heavy chain constant regions comprising a substitution of E225 with K or R, R240 with D or E, or R286 with D or E and the other of the two IgA heavy chain constant regions comprising a substitution of E225 with K or R, R240 with D or E, or R286 with D,
wherein the amino acid numbering corresponds to SEQ ID NO: 2.

3. The dimeric bispecific IgA antibody of claim 1 or claim 2, wherein the correct association of the light chains and their cognate heavy chains is achieved by exchange of heavy-chain and light-chain domains within the antigen binding fragment (Fab) of one half of each bispecific antibody binding unit via crossover of the VH and VL domains.

4. The dimeric bispecific IgA antibody of claim 1 or claim 2, wherein the IgA heavy chain constant regions are IgA1 heavy chain constant regions.

5. The dimeric bispecific IgA antibody of claim 1 or claim 2, wherein the IgA heavy chain constant regions are IgA2 heavy chain constant regions.

6. The dimeric bispecific IgA antibody of claim 1 or claim 2, wherein the J chain comprises the sequence of SEQ ID NO: 3.

7. The dimeric bispecific IgA antibody of claim 2, wherein the heavy chain constant regions are human IgA2 constant regions comprising SEQ ID NO: 4 and SEQ ID NO: 5, respectively, and wherein the light chain constant regions each comprise SEQ ID NO: 6.

8. The dimeric bispecific IgA antibody of claim 3, wherein the heavy chain constant regions are human IgA2 constant regions comprising SEQ ID NO: 4 and SEQ ID NO: 8, respectively, and wherein the light chain constant regions comprise SEQ ID NO: 6 and SEQ ID NO: 9, respectively.

9. The dimeric bispecific IgA antibody of claim 1 or claim 2, which specifically binds to two different antigens of a respiratory syncytial virus (RSV).

10. The dimeric bispecific IgA antibody of claim 9, which binds to RSV F and RSV G.

11. The dimeric bispecific IgA antibody of claim 10, wherein each binding unit comprises the heavy chains SEQ ID NO: 10 and SEQ ID NO: 12, respectively and the light chains SEQ ID NO: 11 and SEQ ID NO: 13, respectively.

12. The dimeric bispecific IgA antibody of claim 1 or claim 2, which specifically binds to two different hemagglutinin (HA) antigens of influenza A virus.

13. The dimeric bispecific IgA antibody of claim 12, wherein each binding unit comprises the heavy chains SEQ ID NO: 14 and SEQ ID NO: 16, respectively and the light chains SEQ ID NO: 15 and SEQ ID NO: 17, respectively.

14. The dimeric bispecific IgA antibody of claim 1 or claim 2, which specifically binds to two different antigens of *Clostridium difficile* (*C. difficile*).

15. The dimeric bispecific IgA antibody of claim 14, which binds to Toxin A and Toxin B of *C. difficile*.

16. The dimeric bispecific IgA antibody of claim 15, wherein each binding unit comprises the heavy chains SEQ ID NO: 18 and SEQ ID NO: 20, respectively and the light chains SEQ ID NO: 19 and SEQ ID NO: 21, respectively.

17. A pharmaceutical composition comprising an effective amount of the dimeric bispecific IgA antibody of claim 1 or claim 2 in admixture with a pharmaceutically acceptable carrier.

* * * * *

UNITED STATES PATENT AND TRADEMARK OFFICE
CERTIFICATE OF CORRECTION

PATENT NO. : 10,822,399 B2
APPLICATION NO. : 15/117432
DATED : November 3, 2020
INVENTOR(S) : Bruce Keyt et al.

It is certified that error appears in the above-identified patent and that said Letters Patent is hereby corrected as shown below:

In the Claims

Column 87, Line 7, Claim 1, replace "with For W; and" with --with F or W; and--

Signed and Sealed this
Fifth Day of January, 2021

Andrei Iancu
*Director of the United States Patent and Trademark Office*